(12) United States Patent
Peralta-Yahya et al.

(10) Patent No.: US 9,376,691 B2
(45) Date of Patent: Jun. 28, 2016

(54) FUSION PROTEINS USEFUL FOR PRODUCING PINENE

(71) Applicant: The Regents of the University of California, Oakland, CA (US)

(72) Inventors: Pamela P. Peralta-Yahya, Atlanta, GA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 101 days.

(21) Appl. No.: 14/091,818

(22) Filed: Nov. 27, 2013

(65) Prior Publication Data

US 2014/0295517 A1 Oct. 2, 2014

Related U.S. Application Data

(60) Provisional application No. 61/730,935, filed on Nov. 28, 2012.

(51) Int. Cl.
| | |
|---|---|
| *C12N 9/88* | (2006.01) |
| *C12N 9/10* | (2006.01) |
| *C07K 19/00* | (2006.01) |
| *C12P 5/00* | (2006.01) |
| *C12N 1/22* | (2006.01) |
| *C12N 1/20* | (2006.01) |
| *C12N 15/52* | (2006.01) |
| *C12N 15/62* | (2006.01) |

(52) U.S. Cl.
CPC . *C12P 5/002* (2013.01); *C12N 1/20* (2013.01); *C12N 1/22* (2013.01); *C12N 9/1085* (2013.01); *C12N 9/88* (2013.01); *C12N 15/52* (2013.01); *C12N 15/62* (2013.01); *C12P 5/007* (2013.01); *C12P 2203/00* (2013.01); *Y02P 20/52* (2015.11)

(58) Field of Classification Search
CPC .......... C12N 15/52; C12N 15/62; C12N 1/20; C12N 1/22; C12N 9/1085; C12N 9/88; C12P 2203/00; C12P 5/002; C12P 5/007
See application file for complete search history.

(56) References Cited

U.S. PATENT DOCUMENTS

| | | | |
|---|---|---|---|
| 2002/0168685 A1* | 11/2002 | Cornish | A61K 47/481 506/4 |
| 2010/0178679 A1 | 7/2010 | Anthony et al. | |
| 2012/0107893 A1* | 5/2012 | Ajikumar | C12P 15/00 435/166 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Burke et al., GenBank accession No. AAN01134, Aug. 29, 2002.*
Schmidt et al., GenBank accession No. ACA21458, Sep. 30, 2010.*
Phillips et al., GenBank accession No. AF543527, Mar. 10, 2003.*
Bohlman et al., GenBank accession No. U87909, Sep. 24, 1997.*
Martin et al., Plant Physiology 135:1908-1927, 2004.*
Harvey et al., Energy Fuels 24:267-273, 2010.*
Conrado et al., Current Opinion in Biotechnology 19:492-499, 2008.*
Hawkins et al., Eur. J. Biochem. 196:717-724, 1991.*
Arora, et al. (2010) Monitoring and analyzing process streams towards understanding ionic liquid pretreatment of switchgrass (*Panicum virgatum* L.). Bioenergy Research 3:134-145.
Atsumi S, Liao JC (2008) Metabolic engineering for advanced biofuels production from *Escherichia coli*. Curr Opin Biotechnol 19:414-419.
Bokinsky et al. (2011) Synthesis of three advanced biofuels from ionic liquid-pretreated switchgrass using engineered *Escherichia coli* Proc Natl Acad Sci USA 108:19949-19954.
Burke et al. (2002) Geranyl diphosphate synthase from Abies grandis: cDNA isolation, functional expression, and characterization. Arch Biochem Biophys 405:130-136.
Deboy RT, et al. (2008) Insights into plant cell wall degradation from the genome sequence of the soil bacterium *Cellvibrio japonicus*. J Bacteriol 190:5455-5463.
Han SJ, Yoo YJ, Kang HS (1995) Characterization of a bifunctional cellulase and its structural gene—the Cel gene of *bacillus* Sp D04 has exoglucanase and endoglucanase activity. J Biol Chem 270:26012-26019.
Martin VJJ, Pitera DJ, Withers ST, Newman JD, Keasling JD (2003) Engineering a mevalonate pathway in *Escherichia coli* for production of terpenoids. Nat Biotechnol 21:796-802.
Phillips et al. (2003) cDNA isolation, functional expression, and characterization of (+)-a-pinene synthase and ( ))-a-pinene synthase from loblolly pine (*Pinus taeda*): Stereocontrol in pinene biosynthesis. 411:267-276.
Qian ZG, Xia XX, Choi JH, Lee SY (2008) Proteome-based identification of fusion partner for high-level extracellular production of recombinant proteins in *Escherichia coli*. Biotechnol Bioeng 101:587-601.
Rixon JE, et al. (1992) Characterization of the gene celd and its encoded product 1,4-beta-D-glucan glucohydrolase-D from *Pseudomonas-fluorescens* subsp *cellulosa*. Biochem J 285:947-955.
Steen EJ, et al. (2010) Microbial production of fatty-acid-derived fuels and chemicals from plant biomass. Nature 463:559-562.

* cited by examiner

*Primary Examiner* — Delia Ramirez
(74) *Attorney, Agent, or Firm* — Robin C. Chiang; Lawrence Berkeley National Laboratory

(57) ABSTRACT

The present invention provides for a modified host cell comprising a heterologous pinene synthase (PS), or enzymatically active fragment or variant thereof, and optionally a geranyl pyrophosphate synthase (GPPS), or enzymatically active fragment or variant thereof, or a fusion protein comprising: (a) a PS and (b) a GPPS linked by a linker.

9 Claims, 15 Drawing Sheets

A pES120:

pButanol:

pPinene:

Production medium

A

B

```
SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Artificial linker designed to link two
      polypeptides

<400> SEQUENCE: 1

Gly Ser Gly Gly Ser Gly
1               5
```

FUSION PROTEINS USEFUL FOR PRODUCING PINENE

RELATED PATENT APPLICATIONS

The application claims priority to U.S. Provisional Patent Application Ser. No. 61/730,935, filed Nov. 28, 2012, which is herein incorporated by reference in its entirety.

STATEMENT OF GOVERNMENTAL SUPPORT

The invention described and claimed herein is made in part utilizing funds supplied by the U.S. Department of Energy under Contract No. DE-AC02-05CH11231. The government has certain rights in this invention.

FIELD OF THE INVENTION

This invention relates generally to biofuel synthesis.

BACKGROUND OF THE INVENTION

The microbial conversion of sustainable lignocellulosic biomass into biofuels could provide a source of fully renewable transportation fuels (1). Generating these fuels from abundant feedstocks such as lignocellulose and cellulosic waste avoids many of the problems associated with current grain-based biofuels, provided the feedstock is responsibly grown and harvested (2). While early efforts toward achieving economical biofuel production have typically focused on improving yields of ethanol made from fermentation of plant sugars (3), recent advances in metabolic engineering have enabled microbial production of fuels that are compatible with existing engines and fuel distribution infrastructure (4, 5). Many of these advances have been made possible by the unparalleled genetic and metabolic tractability of the model bacterium *Escherichia coli* (6, 7). *E. coli* has been engineered to biosynthesize perhaps the most chemically diverse range of chemicals of any organism, including hydrogen (8), higher alcohols (9, 10), fatty-acid based chemicals (11), and terpenes (12, 13). Extensive knowledge of *E. coli* physiology will continue to aid improvements in titers beyond those achieved in proof-of-concept stages toward levels required for a commercial-scale biofuel production process.

Unfortunately, several challenges must be overcome before lignocellulose can be considered an economically competitive feedstock for biofuel production. One of the more significant challenges is the need for large quantities of glycoside hydrolase (GH) enzymes to efficiently convert lignocellulose into fermentable sugars. These enzymes are typically generated in a dedicated process that incurs substantial capital and material expense and represent the second highest contribution to raw material cost after the feedstock itself (1, 14). An alternative approach, known as consolidated bioprocessing, could potentially avoid the costs of a dedicated enzyme generation step by performing it in a combined process that includes biomass hydrolysis and fuel production (FIG. 1A) (15, 16). This can be achieved by incorporating both biomass-degrading and biofuel-producing capabilities into a single organism through genetic engineering. Several microorganisms have been engineered to ferment model cellulosic and hemicellulosic substrates directly into ethanol or other fuels (reviewed in refs. 15 and 17). For example, the yeast *Saccharomyces cerevisiae* (18) and the bacterium *Klebsiella oxytoca* (19) have been modified to convert phosphoric acid swollen cellulose (PASC) directly to ethanol without the addition of exogenous cellulase. However, PASC and similar model substrates are typically prepared using techniques that are neither suitable for actual plant biomass nor feasible on a large scale (20). Furthermore, no biofuel with the combustion properties of petrochemical fuels, which could be used directly in existing infrastructure, has been generated directly from unrefined lignocellulosic biomass.

A cellulolytic strain of *E. coli* capable of growth on plant biomass would be a first step toward producing many varieties of advanced biofuels at lowered cost. One obstacle to engineering *E. coli* for consumption of lignocellulose is the organism's inferior capacity for protein export, which renders it unable to secrete cellulases in quantities required for industrial-scale lignocellulose hydrolysis. Various techniques, developed over decades of research, can be applied to generate secreted yields from *E. coli* of 0.5-0.8 g protein/L (21). Unfortunately, these concentrations are still too low for an industrial process, which are most efficient around levels of 20 mg cellulase/g solids and 200 g/L solids loading (22) [although recent work (23) has demonstrated that removal of soluble hydrolase inhibitors may substantially reduce the enzyme loading required]. To further engineer a cellulolytic *E. coli* strain for use in consolidated bioproces sing, biofuel production pathways must also be introduced and expressed at levels that yield high titers while not overburdening the cell. The integration of engineered cellulolytic capabilities together with pathways for advanced biofuel production into a single organism may present an insurmountable metabolic burden for *E. coli*, or indeed any microbe, without appropriate regulation.

SUMMARY OF THE INVENTION

The present invention provides for a modified host cell comprising a heterologous pinene synthase (PS), or enzymatically active fragment or variant thereof, and optionally a geranyl pyrophosphate synthase (GPPS), or enzymatically active fragment or variant thereof, or a fusion protein of the present invention. Modified host cells are modified by recombinant means. In some embodiments, the PS, or enzymatically active fragment thereof, is or comprises the amino acid of *Artemisia annua, Pinus taeda, Picea abies, Fregaria vesca,* or *Abies grandis* PS. In some embodiments, the GPPS, or enzymatically active fragment thereof, is or comprises the amino acid of *Artemisia annua, Pinus taeda, Picea abies, Abies grandis, Arabidopsis thaliana,* or *Mentha piperita* GPPS. In some embodiments, the PS is α-PS or β-PS. Pinene is synthesized from acetyl-CoA with the expression products of the genes indicated in the pathway shown in FIG. 11. α-PS and β-PS synthesize α-pinene and β-pinene, respectively.

The present invention provides for a fusion protein comprising: (a) a pinene synthase (PS), or enzymatically active fragment or variant thereof, and (b) a geranyl pyrophosphate synthase (GPPS), or enzymatically active fragment or variant thereof, wherein (a) and (b) are linked by a linker. In some embodiments, the linker is a peptide of any suitable number of amino acid residues. In some embodiments, the linker is a peptide of between about 0 and about 20 amino acid residues. In some embodiments, the linker is a peptide of between about 0 and about 10 amino acid residues. In some embodiments, the linker is a peptide of between about 3 and about 9 amino acid residues. In some embodiments, the linker is a peptide of between about 4 and about 8 amino acid residues. In some embodiments, the linker is a peptide of between about 5 and about 7 amino acid residues. In some embodiments, the linker is a peptide of about 6 amino acid residues. In some embodiments, the linker comprises the amino acid sequence GSGGSG (SEQ ID NO:1). In some embodiments, the PS and GPPS are from the same species of organism. In some embodiments, the PS and GPPS are from two different species. In some embodiments, the PS is obtained or derived from *Artemisia annua, Pinus taeda, Picea abies, Fregaria vesca,* or *Abies grandis*. In some embodiments, the GPPS is obtained or derived from *Artemisia annua, Pinus taeda, Picea abies, Abies grandis, Arabidopsis thaliana,* or *Mentha piperita*. In some embodiments, the C-terminus of the PS is linked via the linker to the N-terminus of the GPPS. In some embodiments, the C-terminus of the GPPS is linked via the linker to the N-terminus of the PS.

In a particular embodiment, the C-terminus of the *Picea abies* GPPS is linked via the linker to the N-terminus of the *Picea abies* PS, wherein the linker is a 6 amino acid long peptide.

In a particular embodiment, the C-terminus of the *Pinus taeda* GPPS is linked via the linker to the N-terminus of the *Pinus taeda* PS, wherein the linker is a 6 amino acid long peptide.

In a particular embodiment, the PS is (+) α-pinene synthase (AF543530, *Pinus taeda*).

The present invention provides for a nucleic acid encoding the fusion protein of the present invention. In some embodiments, the nucleic acid is a vector. In some embodiments, the vector is an expression vector. In some embodiments, the nucleic acid comprises one or more promoters operably linked to the open reading frame encoding the fusion protein or enzyme. In some embodiments, the codon usage encoding the enzyme is fully or at least partially codon optimized for the host cell. The nucleic acid can be a vector capable of stable maintenance in the host cell or is stably integrated into a chromosome of the host cell. When more than one enzymes or fusion proteins are present, each is independently either encoded on a vector capable of stable maintenance in the host cell or is stably integrated into a chromosome of the host cell. In some embodiments, more than one enzyme or fusion protein can be encoded on and expressed from one vector.

In some embodiments, the host cell when cultured expresses the GPPS, PS and/or fusion protein, and produces pinene. The host cell can either natively be capable of producing dimethylallyl pyrophosphate (or -diphosphate) (DMAPP), which is converted in pinene by GPPS and PS, or the host cell comprises one or more heterologous genes, or variants thereof, encoding one or more enzymes which convert acetyl CoA into DMAPP (see FIG. 11A).

In some embodiments, the host cell when cultured is capable of producing pinene at yields or levels at least equal to or more than about the yields or levels described herein.

In some embodiments, the host cell further comprises one or more of the genes, or variants thereof, encoding an enzyme that breaks down cellulose or hemicellulose into a sugar that the host cell can use as a sole carbon source. Such enzymes include, but are not limited, to cellulase and endoxylanase. Suitable enzymes are listed in Table 1. In some embodiments, the enzyme is fused with a secretory sequence, such as *E. coli* OsmY, such that upon expression the enzyme is exported to the outside of the host cell.

The pinene produced can be isolated and used as a constituent of jet fuel, or it can be converted further chemically catalyzed in pinene dimers.

The present invention provides for a method for culturing or growing the modified host cell of the present invention, comprising: (a) providing a modified host cell of the present invention in a solution, (b) culturing or growing the modified host cell such that pinene is expressed, (c) optionally isolating or separating the pinene from the solution, (d) optionally chemically catalyzing the pinene to produce a pinene dimer, and (e) optionally using the pinene or pinene dimer as a fuel. In some embodiments, the solution comprises a biomass comprising a cellulose and/or hemicellulose as a carbon source, and the host cell expresses one or more enzymes capable of breaking down the cellulose and/or hemicellulose.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
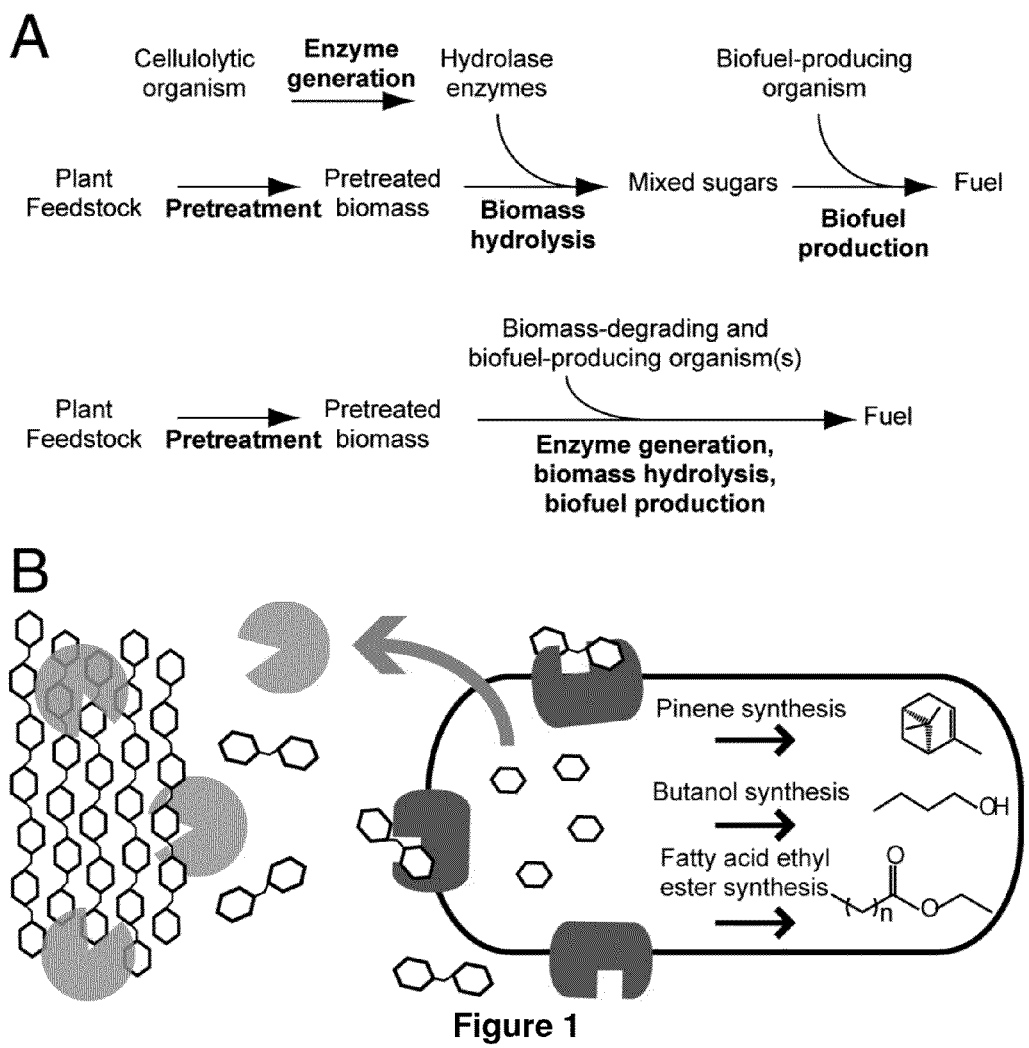
FIG. 1. Consolidated bioprocessing of plant biomass into biofuels by *E. coli*. (A) Two processes for biofuel production. Typically, cellulase and hemicellulase enzymes are produced in a process step separate from biomass hydrolysis and biofuel production (top). Consolidated bioprocessing (bottom) combines enzyme generation, biomass hydrolysis, and biofuel production into a single stage. (B) Engineering *E. coli* for use in consolidated bioprocessing. Cellulose and hemicellulose are hydrolyzed by secreted cellulase and hemicellulose enzymes (cyan) into soluble oligosaccharides. β-glucosidase enzymes (red) further hydrolyze the oligosaccharides into monosaccharides, which are metabolized into biofuels via heterologous pathways.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an enzyme" includes a plurality of such enzymes, and so forth.

In this specification and in the claims that follow, reference will be made to a number of terms that shall be defined to have the following meanings:

The terms "expression vector" or "vector" refer to a compound and/or composition that can be introduced into a host cell by any suitable method, including but not limited to transduction, transformation, transfection, infection, electroporation, conjugation, and the like; thereby causing the cell to express nucleic acids and/or proteins other than those native to the cell, or in a manner not native to the cell. An "expression vector" contains a sequence of nucleic acids (ordinarily RNA or DNA) to be expressed by the host cell. Optionally, the expression vector also comprises materials to aid in achieving entry of the nucleic acid into the host cell, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host cell and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

As used herein, the terms "nucleic acid", "nucleotide" and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing normucleotidic backbones, provided that the polymers contain nucleobases in a configuration that allows for base pairing and base stacking, as found in DNA and RNA.

The term "operably linked" refers to a functional linkage between a nucleic acid expression control sequence (such as a promoter) and a second nucleic acid sequence, wherein the expression control sequence directs transcription of the nucleic acid corresponding to the second sequence.

An enzyme or polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

These and other objects, advantages, and features of the invention will become apparent to those persons skilled in the art upon reading the details of the invention as more fully described below.

The suitable variants of the enzymes include the alleles, variants, and mutants of any of the enzymes, such as those described herein, that comprise an amino acid sequence having at least 70%, 80%, 90%, 95%, or 99% identity as compared to the amino acid sequence of the wild-type enzymes, and is able to catalyze the desired enzymatic reaction.

The nucleic acid used in the present invention can be a recombinant nucleic acid. The recombinant nucleic acid can be a double-stranded or single-stranded DNA. The recombinant nucleic acid can also comprise promoter sequences for transcribing the enzyme(s) or one or more enzymes for producing pinene in the host cell. The recombinant nucleic acid can also comprise sequences sufficient for having the recombinant nucleic acid stably replicate in the host cell. The recombinant nucleic acid can be a replicon capable of stable maintenance in the host cell. In some embodiments, the replicon is a vector or expression vector, or a plasmid.

In some embodiments of the invention, the gene(s) are operatively linked to a promoter that produces constitutive expression or is modulated, such as modulated by the amount or concentration of the organic molecule or a precursor of the organic molecule in the host cell. The gene(s) can be operatively linked to promoters and control elements that modulate the expression of the enzyme.

In some embodiments of the invention, the host cell is a Gram-negative bacterium. In some embodiments of the invention, the host cell is a proteobacteria bacterium. In some embodiments of the invention, the bacterium is an enteric bacterium. In some embodiments of the invention, the bacterium is of the genus *Planctomyces*, *Bradyrhizobium*, *Rhodobacter*, *Rhizobium*, *Myxococcus*, *Klebsiella*, *Azotobacter*, *Escherichia*, *Salmonella*, *Pseudomonas*, *Caulobacter*, *Chlamydia*, *Acinetobacter*, *Sinorhizobium*, *Vibrio*, or *Zymomonas*. In some embodiments of the invention, the bacterium is *E. coli*. In some embodiments, the host cell is a species that in nature does not have PS and/or GPPS.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in the host cells and those that remain episomal or those that integrate into the host cell genome.

The vectors may be chosen to contain control sequences operably linked to the resulting coding sequences in a manner that expression of the coding sequences may be effected in an appropriate host cell. Suitable control sequences include those that function in the host cells. If the cloning vectors employed to obtain encoded peptides of interest lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control elements include promoters, optionally containing operator sequences, and other elements depending on the nature of the host, such as ribosome binding sites. Particularly useful promoters for host cells include those promoters that are native to the peptide of interest. However, other bacterial promoters, such as those derived from sugar metabolizing enzymes, such as galactose, lactose (lac) and maltose, are also useful. Additional examples include promoters derived from biosynthetic enzymes such as for tryptophan (tip), the β-lactamase (bla), bacteriophage lambda PL, and T5. In addition, synthetic promoters, such as the tac promoter (U.S. Pat. No. 4,551,433; hereby incorporated by reference), can be used.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The nucleic acid sequences or nucleotide sequences described herein, or a mixture of such sequences, can be cloned into one or more recombinant vectors as individual cassettes, with separate control elements or under the control of a single promoter. Methods for introducing the nucleic acid into suitable host cells are known to those of skill in the art and typically include the use of $CaCl_2$ or other agents, such as divalent cations, lipofection, DMSO, protoplast transformation, conjugation, and electroporation.

REFERENCES CITED

1. National Research Council (U.S.) (2009) Panel on alternative liquid transportation fuels. Liquid Transportation Fuels from Coal and Biomass: Technological Status, Costs, and Environmental Impacts (Natl Academies Press, Ishington) p 370.
2. Tilman D, et al. (2009) Beneficial biofuels—the food, energy, and environment trilemma. Science 325:270-271.
3. Ingram L O, et al. (1999) Enteric bacterial catalysts for fuel ethanol production. Biotechnol Prog 15:855-866.
4. Fortman J L, et al. (2008) Biofuel alternatives to ethanol: pumping the microbial well. Trends Biotechnol 26:375-381.
5. Keasling J D (2010) Manufacturing molecules through metabolic engineering. Science 330:1355-1358.
6. Atsumi S, Liao J C (2008) Metabolic engineering for advanced biofuels production from *Escherichia coli*. Curr Opin Biotechnol 19:414-419.
7. Clomburg J M, Gonzalez R (2010) Biofuel production in *Escherichia coli*: The role of metabolic engineering and synthetic biology. Appl Microbiol Biotechnol 86:419-434.
8. Maeda T, Sanchez-Torres V, Wood T K (2007) Enhanced hydrogen production from glucose by metabolically engineered *Escherichia coli*. Appl Microbiol Biotechnol 77:879-890.
9. Atsumi S, et al. (2008) Metabolic engineering of *Escherichia coli* for 1-butanol production. Metab Eng 10:305-311.
10. Atsumi S, Hanai T, Liao J C (2008) Non-fermentative pathways for synthesis of branched-chain higher alcohols as biofuels. Nature 451:86-89.
11. Steen E J, et al. (2010) Microbial production of fatty-acid-derived fuels and chemicals from plant biomass. Nature 463:559-562.
12. Peralta-Yahya P P, et al. (2011) Identification and microbial production of a terpenebased advanced biofuel. Nat Commun 2:483, 10.1038/ncomms1494.
13. Wang C, et al. (2010) Farnesol production from *Escherichia coli* by harnessing the exogenous mevalonate pathway. Biotechnol Bioeng 107:421-429.
14. Blanch H W, Klein-Marcuschamer D, Oleskowicz-Popiel P, Simmons B A (2010) Technoeconomic analysis of biofuels: A wiki-based platform for lignocellulosic biorefineries. Biomass Bioenergy 34:1914-1921.
15. Lynd L R, van Zyl W H, McBride J E, Laser M (2005) Consolidated bioprocessing of cellulosic biomass: An update. Curr Opin Biotechnol 16:577-583.
16. Lynd L R, Weimer P J, van Zyl W H, Pretorius I S (2002) Microbial cellulose utilization: Fundamentals and biotechnology. Microbiol. Mol Biol Rev 66:506-577.
17. la Grange D C, den Haan R, van Zyl W H (2010) Engineering cellulolytic ability into bioprocessing organisms. Appl Microbiol Biotechnol 87:1195-1208.
18. Den Haan R, Rose S H, Lynd L R, van Zyl W H (2007) Hydrolysis and fermentation of amorphous cellulose by recombinant *Saccharomyces cerevisiae*. Metab Eng 9:87-94.
19. Zhou S D, Ingram L O (2001) Simultaneous saccharification and fermentation of amorphous cellulose to ethanol by recombinant *Klebsiella oxytoca* SZ21 without supplemental cellulase. Biotechnol Lett 23:1455-1462.
20. Alvira P, Tomas-Pejo E, Ballesteros M, Negro M J (2010) Pretreatment technologies for an efficient bioethanol production process based on enzymatic hydrolysis: A review. Bioresour Technol 101:4851-4861.
21. Georgiou G, Segatori L (2005) Preparative expression of secreted proteins in bacteria: Status report and future prospects. Curr Opin Biotechnol 16:538-545.
22. Stickel J J, Roche C M, Dibble C J, Knutsen J S, Liberatore M W (2009) Particle concentration and yield stress of biomass slurries during enzymatic hydrolysis at high-solids loadings. Biotechnol Bioeng 104:290-300.
23. Ladisch M R, Kim Y, Ximenes E, Mosier N S (2011) Soluble inhibitors/deactivators of cellulase enzymes from lignocellulosic biomass. Enzyme Microb Technol 48:408-415.
24. Klein-Marcuschamer D, Simmons B A, Blanch H W (2011) Techno-economic analysis of a lignocellulosic ethanol biorefinery with ionic liquid pre-treatment. Biofuel Bioprod Bior 5:562-569.
25. Li C L, et al. (2010) Comparison of dilute acid and ionic liquid pretreatment of switchgrass: Biomass recalcitrance, delignification and enzymatic saccharification. Bioresour Technol 101:4900-4906.
26. Qian Z G, Xia X X, Choi J H, Lee S Y (2008) Proteome-based identification of fusion partner for high-level extracellular production of recombinant proteins in *Escherichia coli*. Biotechnol Bioeng 101:587-601.
27. Han S J, Yoo Y J, Kang H S (1995) Characterization of a bifunctional cellulase and its structural gene—the Cel gene of *Bacillus* Sp D04 has exoglucanase and endoglucanase activity. J Biol Chem 270:26012-26019.

28. Singh S, et al. (2010) Monitoring and analyzing process streams towards understanding ionic liquid pretreatment of switchgrass (Panicum virgatum L.). Bioenergy Research 3:134-145.
29. Deboy R T, et al. (2008) Insights into plant cell wall degradation from the genome sequence of the soil bacterium Cellvibrio japonicus. J Bacteriol 190:5455-5463.
30. Rixon J E, et al. (1992) Characterization of the gene celd and its encoded product 1,4-beta-D-glucan glucohydrolase-D from Pseudomonas-fluorescens subsp cellulosa. Biochem J 285:947-955.
31. Zaslayer A, et al. (2006) A comprehensive library of fluorescent transcriptional reporters for Escherichia coli. Nat Methods 3:623-628.
32. Keseler I M, et al. (2009) EcoCyc: A comprehensive view of Escherichia coli biology. Nucleic Acids Res 37:D464-D470.
33. Georgiou G, Shuler M L, Wilson D B (1988) Release of periplasmic enzymes and other physiological-effects of beta-lactamase overproduction in Escherichia-coli. Biotechnol Bioeng 32:741-748.
34. Antizar-Ladislao B, Turrion-Gomez J L (2008) Second-generation biofuels and local bioenergy systems. Biofuels Bioprod Bior 2:455-469.
35. Harvey B G, Wright M E, Quintana R L (2010) High-density renewable fuels based on the selective dimerization of pinenes. Energy Fuels 24:267-273.
36. Hess M, et al. (2011) Metagenomic discovery of biomass-degrading genes and genomes from cow rumen. Science 331:463-467.
37. Rinaldi R, Engel P, Buchs J, Spiess A C, Schuth F (2010) An integrated catalytic approach to fermentable sugars from cellulose. Chemsuschem 3:1151-1153.
38. Cantarel B L, et al. (2009) The Carbohydrate-Active EnZymes database (CAZy): An expert resource for glycogenomics. Nucleic Acids Res 37:D233-D238.
39. Edgar R C (2004) MUSCLE: Multiple sequence alignment with high accuracy and high throughput. Nucleic Acids Res 32:1792-1797.
40. Bingham J, Sudarsanam S (2000) Visualizing large hierarchical clusters in hyperbolic space. Bioinformatics 16:660-661.
41. Villalobos A, Ness J E, Gustafsson C, Minshull J, Govindarajan S (2006) Gene Designer: a synthetic biology tool for constructing artificial DNA segments. BMC Bioinformatics 7:285.
42. Datsenko K A, Wanner B L (2000) One-step inactivation of chromosomal genes in Escherichia coli K-12 using PCR products. Proc Natl Acad Sci USA 97:6640-6645.
43. Anderson J C, et al. (2010) BglBricks: A flexible standard for biological part assembly. J Biol Eng 4:1.
44. Li M Z, Elledge S J (2007) Harnessing homologous recombination in vitro to generate recombinant DNA via SLIC. Nat Methods 4:251-256.
45. Dunlop M J, Cox R S, Levine J H, Murray R M, Elowitz M B (2008) Regulatory activity revealed by dynamic correlations in gene expression noise. Nat Genet. 40:1493-1498.
46. Gibson D G, et al. (2009) Enzymatic assembly of DNA molecules up to several hundred kilobases. Nat Methods 6:343-345.
47. Horton R M, Hunt H D, Ho S N, Pullen J K, Pease L R (1989) Engineering hybrid genes without the use of restriction enzymes—gene-splicing by overlap extension. Gene 77:61-68.
48. Steen E J, et al. (2010) Microbial production of fatty-acid-derived fuels and chemicals from plant biomass. Nature 463:559-562.
49. Salis H M, Mirsky E A, Voigt C A (2009) Automated design of synthetic ribosome binding sites to control protein expression. Nat Biotechnol 27:946-950.
50. Martin V J J, Pitera D J, Withers S T, Newman J D, Keasling J D (2003) Engineering a mevalonate pathway in Escherichia coli for production of terpenoids. Nat Biotechnol 21:796-802.
51. Zhang Y H P, Cui J B, Lynd L R, Kuang L R (2006) A transition from cellulose swelling to cellulose dissolution by o-phosphoric acid: Evidence from enzymatic hydrolysis and supramolecular structure. Biomacromolecules 7:644-648.

The above references are incorporated by reference.

The invention having been described, the following examples are offered to illustrate the subject invention by way of illustration, not by way of limitation.

Example 1

Synthesis of Three Advanced Biofuels from Ionic Liquid-Pretreated Switchgrass Using Engineered *Escherichia coli*

One approach to reducing the costs of advanced biofuel production from cellulosic biomass is to engineer a single microorganism to both digest plant biomass and produce hydrocarbons that have the properties of petrochemical fuels. Such an organism would require pathways for hydrocarbon production and the capacity to secrete sufficient enzymes to efficiently hydrolyze cellulose and hemicellulose. To demonstrate how one might engineer and coordinate all of the necessary components for a biomass-degrading, hydrocarbon-producing microorganism, a microorganism naïve to both processes, *Escherichia coli*, is engineered to grow using both the cellulose and hemicellulose fractions of several types of plant biomass pretreated with ionic liquids. The engineered strains express cellulase, xylanase, beta-glucosidase, and xylobiosidase enzymes under control of native *E. coli* promoters selected to optimize growth on model cellulosic and hemicellulosic substrates. Furthermore, these strains grow using either the cellulose or hemicellulose components of ionic liquid-pretreated biomass or on both components when combined as a coculture. Both cellulolytic and hemicellulolytic strains are further engineered with three biofuel synthesis pathways to demonstrate the production of fuel substitutes or precursors suitable for gasoline, diesel, and jet engines directly from ionic liquid-treated switchgrass without externally supplied hydrolase enzymes. This demonstration represents a major advance toward realizing a consolidated bioprocess. With improvements in both biofuel synthesis pathways and biomass digestion capabilities, this approach could provide an economical route to production of advanced biofuels.

*E. coli* is engineered to convert plant biomass into three advanced biofuels without the addition of exogenous GH enzymes (FIG. 1B). The carefully regulated expression of heterologous GH enzymes made suitable for export by *E. coli* allows rapid and efficient growth on model cellulosic and hemicellulosic substrates, as well as on the cellulose and hemicellulose components of raw plant biomass pretreated with ionic liquids (IL). IL pretreatment of plant biomass is a promising approach for enabling efficient biomass conversion (20). While the price of IL is currently a substantial barrier to commercialization, performance targets have been identified that could eventually enable adoption of this highly effective pretreatment technology (24). Unlike other pretreatment techniques, dissolution of plant biomass in IL nearly eliminates cellulose crystallinity and significantly decreases lignin content, thereby significantly decreasing the enzyme load required for hydrolysis (25). The present *E. coli* is capable of growing on the cellulose and hemicellulose fractions of several types of IL-pretreated plant biomass, even with low yields of secreted protein (<0.1 mg enzymes/g solids). Furthermore, it is shown that cellulolytic and hemicellulolytic capabilities can be expressed with any of three distinct biofuel synthesis pathways in the same organism. By using cocultures of fuel-producing cellulolytic and hemicellulolytic strains, the production of fuel substitutes or precursors suitable for three engine types (gasoline, diesel, jet) directly from both the cellulose and hemicellulose components of IL-treated switchgrass is demonstrated. This represents a major advance toward combining the extensive biosynthetic capabilities of *E. coli* with lignocellulose utilization, while avoiding a dedicated process for enzyme generation, a substantial cost barrier to advanced biofuel production. These results are a proof-of-concept that provides the foundation to further developments in both *E. coli* engineering and IL pretreatment that could eventually realize the cost savings achievable by consolidated bioprocessing. The modifications described here could likely be transplanted into other industrial microorganisms.

Results

Figure 5:
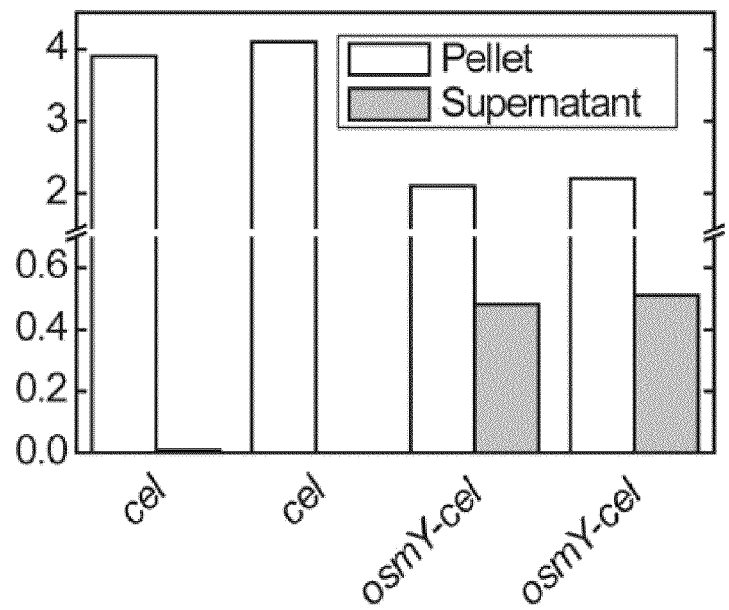
FIG. 5. N-terminal fusion of the E. coli protein OsmY with the Cel cellulase increases levels of extracellular cellulase activity relative to Cel alone. E. coli MG1655 cells bearing plasmids expressing either osmY-cel or cel under control of the PcspD promoter are grown in LB medium with 100 µg/mL carbenicillin for 24 h. One-mL culture samples are centrifuged and the growth medium removed. The cell pellet is lysed and azo-CMC assays are performed on both the lysate and the culture medium.
Figure 6:
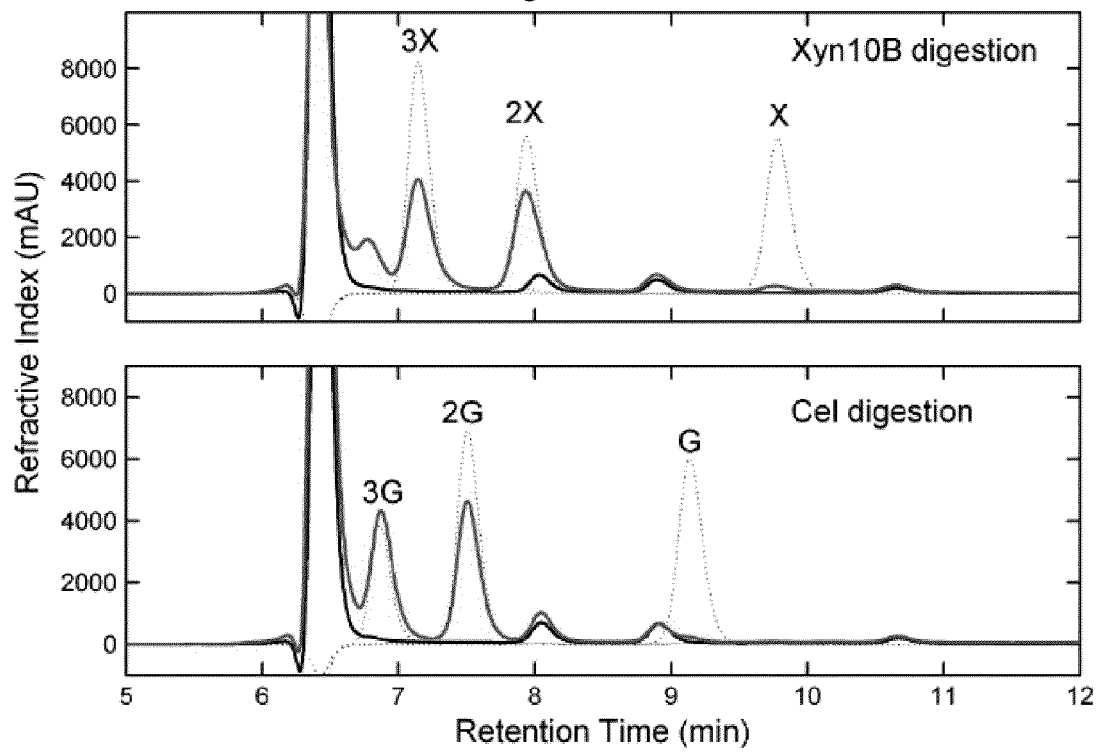
FIG. 6. The endocellulase Cel and the endoxylanase Xyn10B both hydrolyse IL-treated switchgrass. 10 mL MOPS-M9 with 3.4% IL-treated switchgrass is treated with either OsmY-Cel or OsmY-Xyn10B at 37° C. with agitation for 4 days. Soluble sugars released by hydrolysis are detected using HPLC. Chromatogram traces of the digestion reaction with OsmY-Xyn10B (top) or OsmY-Cel (bottom) with pre-digestion (black) and postdigestion (red) traces are shown. Peaks of standards are shown as dashed traces. Peaks indicated are xylotriose (3×), xylobiose (2×), and xylose (X), cellotriose (3G), cellobiose (2G), and glucose (G).

The first step of lignocellulose metabolism is hydrolysis of cellulose and hemicellulose by secreted cellulase and hemicellulase enzymes, respectively (FIG. 1B). It has been previously found that the *Clostridium stercorarium* endoxylanase Xyn10B can be produced extracellularly by *E. coli* when fused with the protein OsmY (11), a fusion shown to enable protein export (26). To find a cellulase exportable by *E. coli*, a library of 10 family 5 endocellulases as fusions with OsmY (Table 1) is expressed. Expression of two of the OsmY-cellulase fusions generated endocellulase activity in the growth medium (FIG. 2A and FIG. 5), with the Cel enzyme from *Bacillus* sp. D04 (cellulase #7) (27) demonstrating the highest activity. Both Cel and Xyn10B demonstrated activity against IL-treated switchgrass, indicating that enzymes expressed extracellularly by *E. coli* could potentially reduce or eliminate the need for exogenously added cellulolytic enzymes. Extracellular OsmY-Cel released glucose equivalent to 5% of the cellulose, producing cellotriose and cellobiose, while OsmY-Xyn10B hydrolyzed 11% of the xylan, mostly into xylotriose and xylobiose (FIG. 6). The combined biomass hydrolysis yield represents 8% of the total sugars available in the IL-treated switchgrass (28).

TABLE 1

Figure 2:
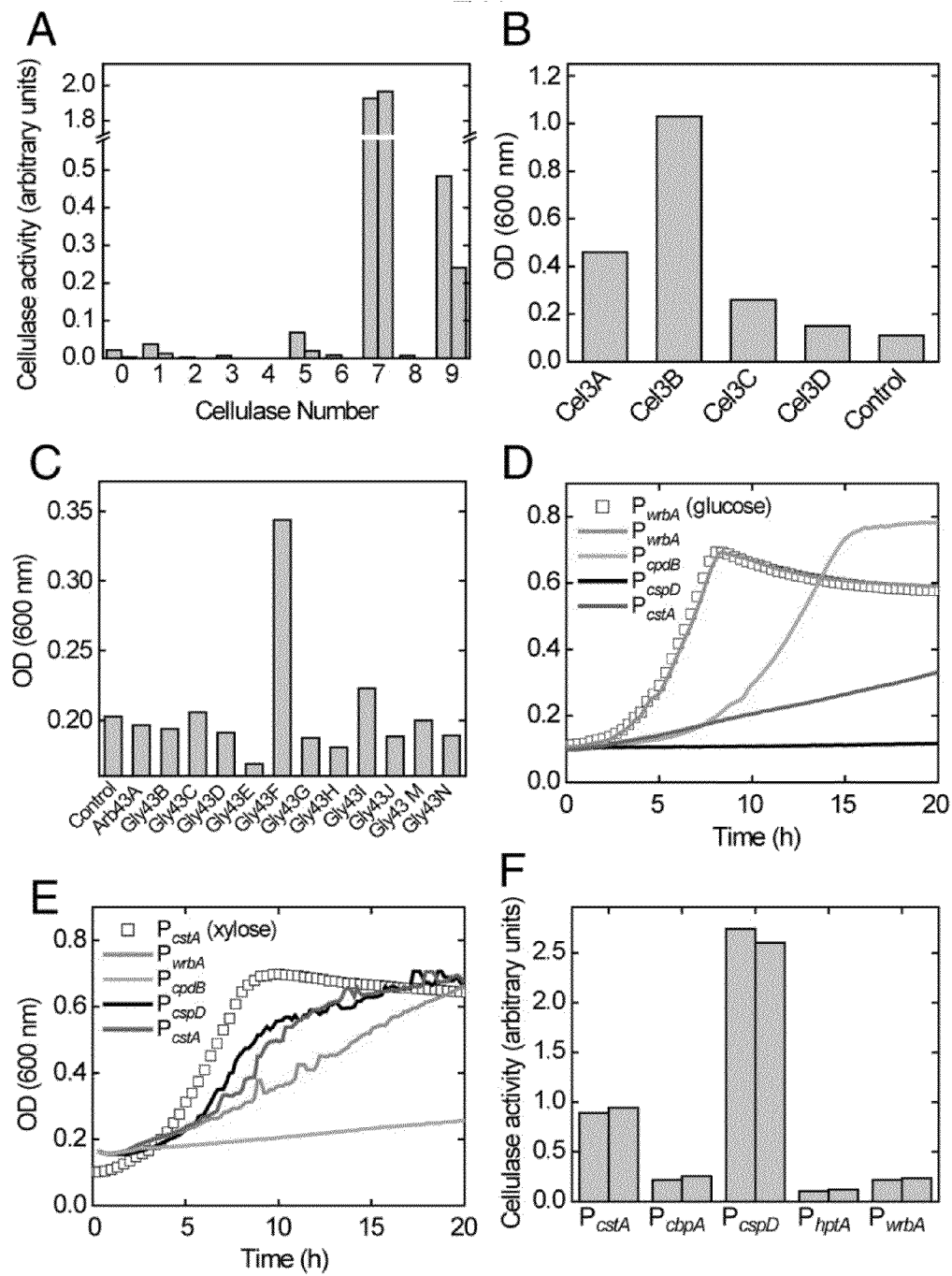
FIG. 2. Assembling biological parts required for lignocellulose hydrolysis and consumption by *E. coli*. (A) Secretion of cellulases. Cellulases are expressed as fusions with the OsmY protein, and extracellular cellulase activity measured using an azo-CMC assay. Cellulase identities that correspond to the numbers used can be found in Table 1. Two measurements from each cellulase are shown. (B) Growth after 18 h in M9/0.2% cellobiose medium of *E. coli* expressing four β-glucosidases from *Cellvibrio japonicus* under control of the lacUV5 promoter. (C) Growth of *E. coli* in MOPS-M9/0.2% xylodextrins after 15 h, enabled by expression of xylobiosidases. (D) Growth curves on MOPS-M9/0.5% cellobiose medium when expressing β-glucosidase Cel3A under control of *E. coli* promoters. A growth curve on glucose is shown for comparison. (E) Growth curves on enzymatically hydrolyzed xylan of *E. coli* expressing the xylobiosidase Gly43F under control of *E. coli* promoters, with a growth curve on xylose for comparison. Each curve is an average of two separate experiments. For growth curves on glucose and xylose, half of the data points are omitted for clarity. (F) Extracellular endocellulase activity levels of cellulase #7 (Cel from *Bacillus* sp.D04) when expressed under the control of several native *E. coli* promoters after 20 h of growth in LB medium. Measurements from biological duplicates are shown.

Key to cellulase numbers in FIG. 2A

| Cellulose No. | Source Organism | Uniprot ID |
|---|---|---|
| 0 | *Xylella fastidiosa* 9a5c | Q9PF60 |
| 1 | *Aspergillus niger* IFO 31125 | Q9C3Z7 |
| 2 | *Epidinium caudatum* | Q9XXV3 |
| 3 | *Macrophomina phaseolina* | Q12637 |
| 4 | *Globodera rostochiensis* | O44078 |
| 5 | *Cellvibrio mixtus* | O07652 |
| 6 | Unknown thermophilic bacterium grown on lignocellulose | Q60054 |
| 7 | *Bacillus* sp. D04 | Q45430 |
| 8 | *Neocallimastix patriciarum* | O59943 |
| 9 | *Prevotella ruminicola* | O06842 |

The soluble oligosaccharides that are produced by enzymatic hydrolysis of cellulose and xylan (cellodextrins and xylodextrins, respectively) cannot be metabolized by *E. coli* MG1655. To further hydrolyze cellodextrins into glucose, four β-glucosidases cloned from *Cellvibrio japonicus*, a Gram-negative cellulolytic bacterium, is screened and determined if their expression in *E. coli* could permit growth on cellobiose (FIG. 1B) (29, 30). *E. coli* grows best on cellobiose when expressing either cel3A or cel3B (FIG. 2B). To enable growth of *E. coli* on xylodextrins, the oligosaccharide products of xylan hydrolysis, 12 xylobiosidase genes from *C. japonicus* (29) is screened. Expression of gly43F enables growth on enzymatically hydrolyzed beechwood xylan (FIG. 2C).

Figure 7:
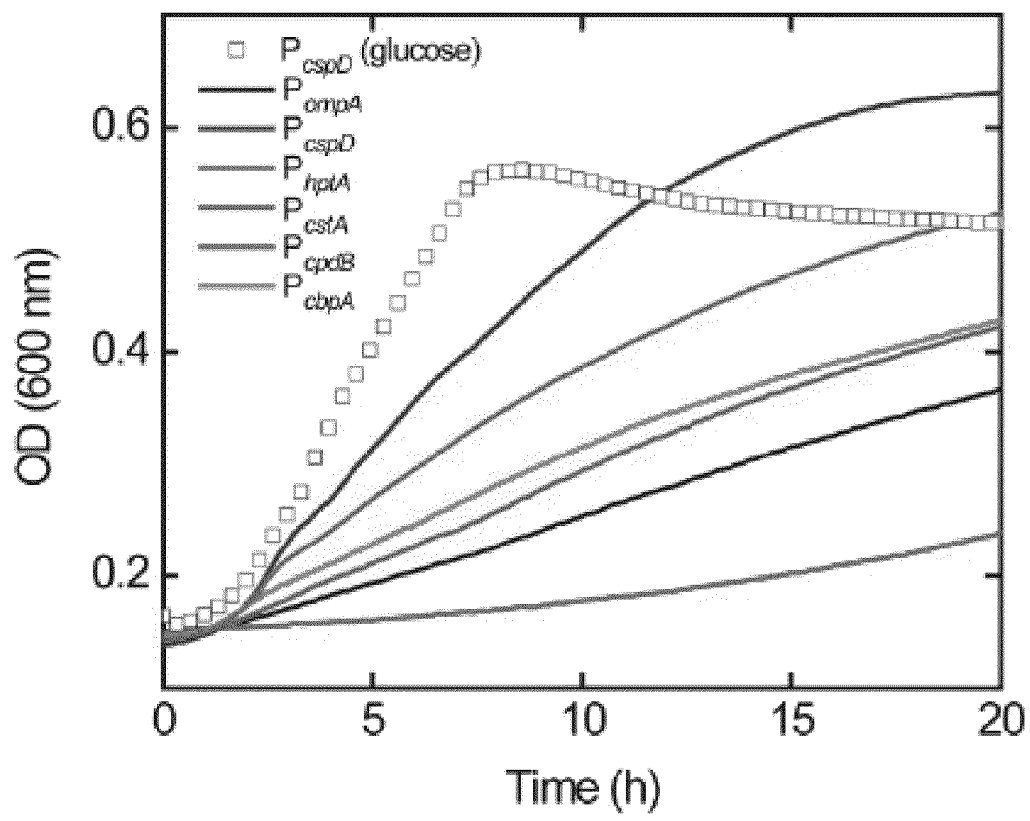
FIG. 7. Growth curves on cellobiose by E. coli expressing C. japonicus beta-glucosidase Cel3B under control of E. coli promoters. Cells are inoculated 125 from cultures grown overnight in LB medium with 100 µg/mL carbenicillin into 100 µL M9/0.2% cellobiose medium with 200 µg/mL carbenicillin. A growth curve on M9/0.2% glucose medium with 200 µg/mL carbenicillin is shown for comparison. Growth is monitored using a 96-well plate at 37° C. in a microplate reader (TECAN). Only half of the data points in the glucose curve are shown for clarity.

The need for exogenously added chemicals to activate expression of biomass-consumption pathways might require extensive optimization of both the timing of induction and the induction strength, complicating engineering of biofuel generation from biomass. Therefore, native *E. coli* promoters to control expression of the selected β-glucosidase and xylobiosidase genes is used. This places expression of the biomass-consumption pathways under control of environmentally responsive promoters and avoids the costs of expensive chemical inducers for activation of the biomass-consumption pathways. It is sought to achieve growth rates of oligosaccharide-utilizing *E. coli* that matched rates observed on the corresponding monosaccharide. Reasoning that expression of biomass-consumption pathways should be limited to periods when *E. coli* is starved of carbon (for instance, when the cells are freshly inoculated into biomass-containing medium from a glucose-based seed culture), several promoters that have been shown to increase in transcriptional activity prior to stationary phase (31) or known to be activated by the gene regulator CRP (32) are screened. cel3A and cel3B are expressed using several native *E. coli* promoters to determine which promoter-enzyme combination would permit the fastest growth on cellobiose. Remarkably, a strain expressing cel3A under the control of the wrbA promoter ($P_{wrbA}$) grows on cellobiose as fast as on glucose (FIG. 2D and FIG. 7). The same set of promoters to optimize expression of gly43F as determined by growth on xylodextrins is screened. It is found that expression of gly43F using the promoters $P_{cstA}$ or $P_{cspD}$ enables a growth rate on xylodextrins nearly as high as on xylose (FIG. 2E). Surprisingly, the use of native promoters to drive expression of appropriate β-glucosidase and xylobiosidase genes enables *E. coli* to grow on oligosaccharides at a rate limited only by the consumption rate of the monosaccharides and perhaps as fast as native cellulolytic organisms.

Figure 3:
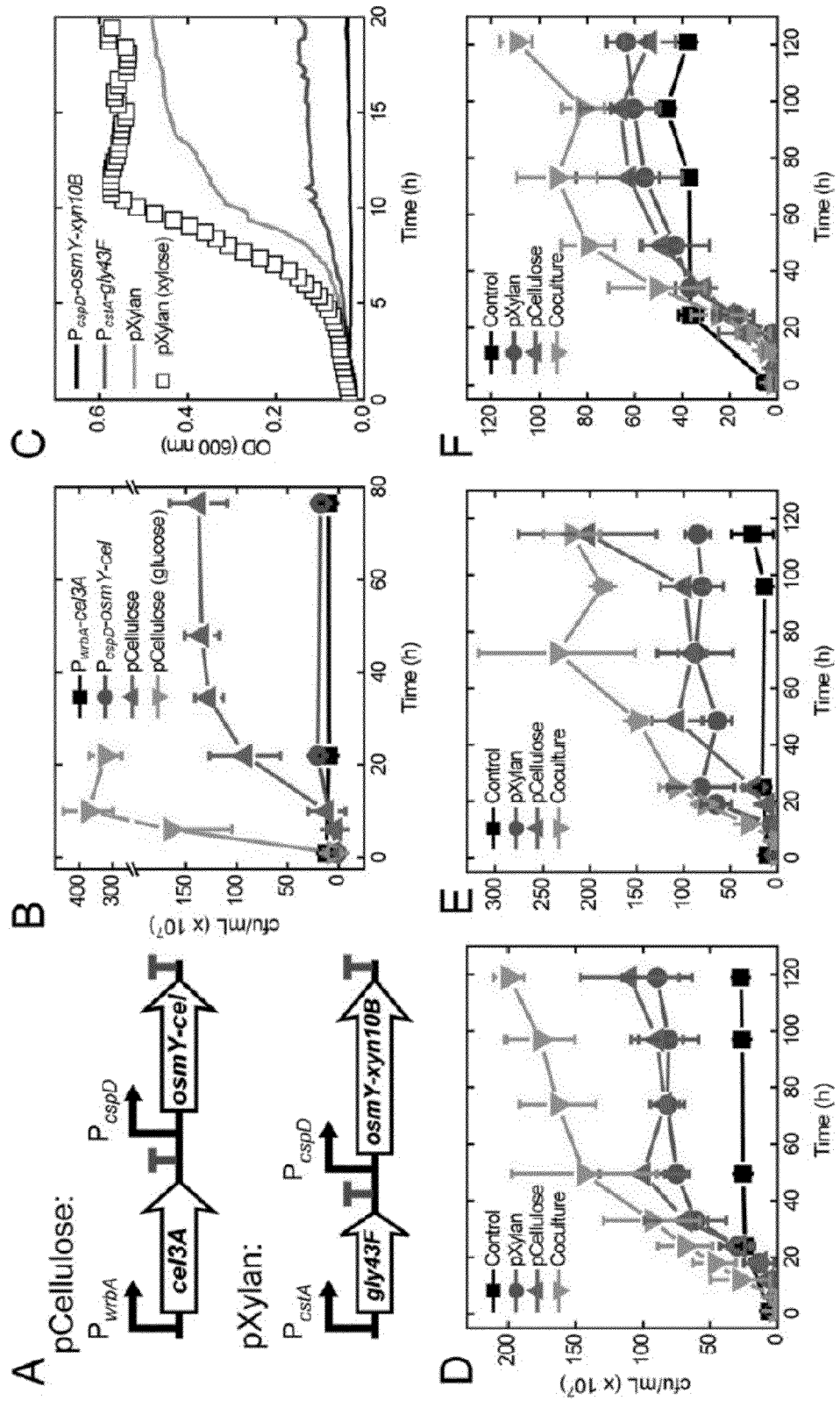
FIG. 3. Engineered *E. coli* grows on model cellulosic substrates and IL-treated plant biomass. (A) Gene schematics for the pCellulose and pXylan plasmids, designed to enable *E. coli* to metabolize cellulose and xylan, respectively. (B) Growth on phosphoric acid swollen cellulose (PASC) monitored by serial dilution, plating, and colony counting. Cells expressing either Cel3A or OsmY-Cel alone, or containing the pCellulose plasmid, are grown in MOPS-M9/0.7% PASC. Growth of the pCellulose-bearing strain in MOPS-M9/0.4% glucose is shown for comparison. (C) Growth of strains expressing either Gly43F or OsmY-XynB alone, or bearing pXylan in MOPS-M9/0.5% beechwood xylan. Growth of pXylan-bearing strain in 0.5% xylose is shown for comparison. Each curve is an average of three separate growth experiments. (D-F) Growth on the cellulose and hemicellulose fractions of IL-treated switchgrass, eucalyptus, and yard waste, respectively. Error bars represent standard deviation of biological triplicates, except for yard waste control strain (biological duplicates).
Figure 8:
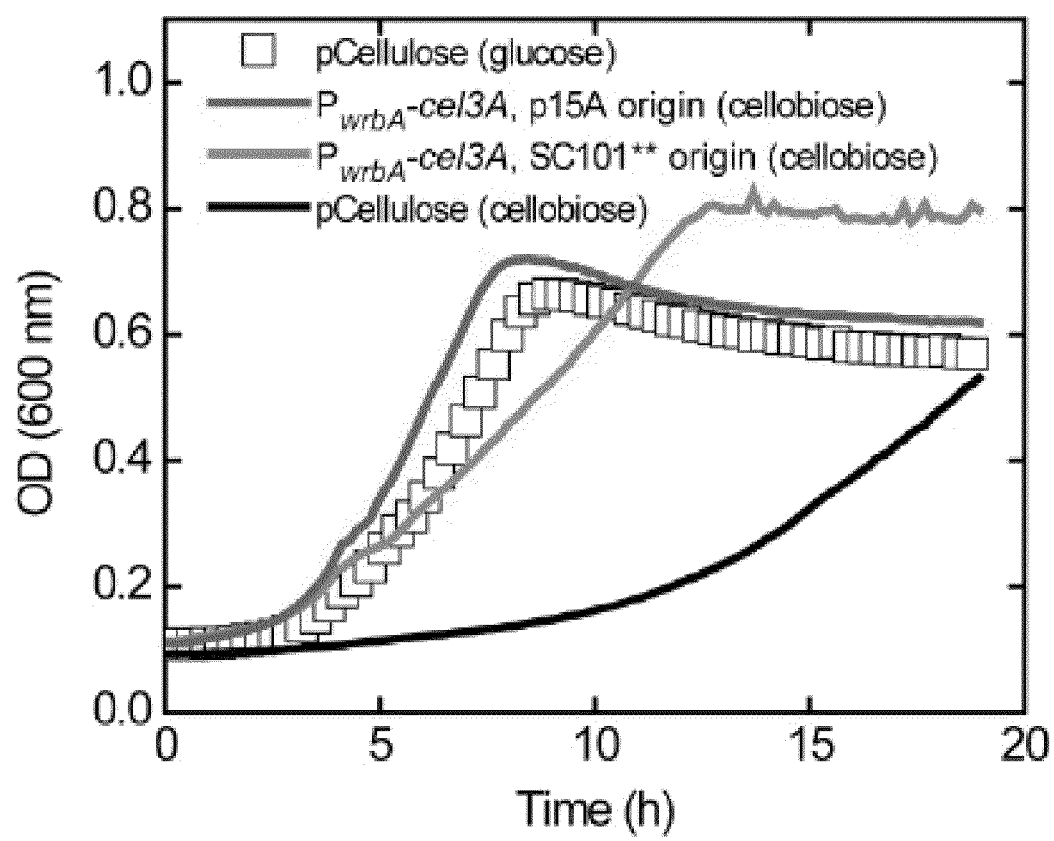
FIG. 8. Growth curves of MG1655 cells bearing plasmidswith PwrbA-cel3A only (with p15A or SC101_ origin of replication) or pCellulose inoculated 1/40 from overnight cultures in LB medium into MOPS-M9/0.5% glucose or cellobiose. Comparison of the growth curves of the strains bearing plasmids with PwrbA-cel3A only suggest that the reduced growth rate of pCellulose on cellobiose is partially due to the lower copy number of the pCellulose plasmid. Each curve is an average of three biological replicates. Only half of the data points in the glucose curve are shown for clarity.

To express the complete biomass conversion pathways under native promoters rather than the chemically inducible promoter used to screen the cellulase library, expression of the osmY-cel fusion is placed under control of the members of our promoter library to determine which promoter generated the maximum extracellular cellulase yield. Expression of osmY-cel using the promoter for the cspD gene ($P_{cspD}$) resulted in the highest cellulase activity of the promoters tested (FIG. 2F). $P_{cspD}$-osmY-cel is combined with $P_{wrbA}$-cel3A into a single plasmid designated pCellulose (FIG. 3A) to enable growth on cellulose. *E. coli* bearing pCellulose grew on the model substrate PASC as the sole carbon source (FIG. 3B), though growth on cellobiose is slowed relative to plasmids bearing $P_{wrbA}$-cel3A P alone (FIG. 8). In the same manner, xyn10B is combined with $P_{cstA}$-gly43F into a single plasmid, designated pXylan (FIG. 3A). Impressively, *E. coli* bearing pXylan grows on beechwood xylan, a model hemicellulosic substrate, at nearly the limit set by the consumption rate of xylose (FIG. 3C).

Figure 9A:
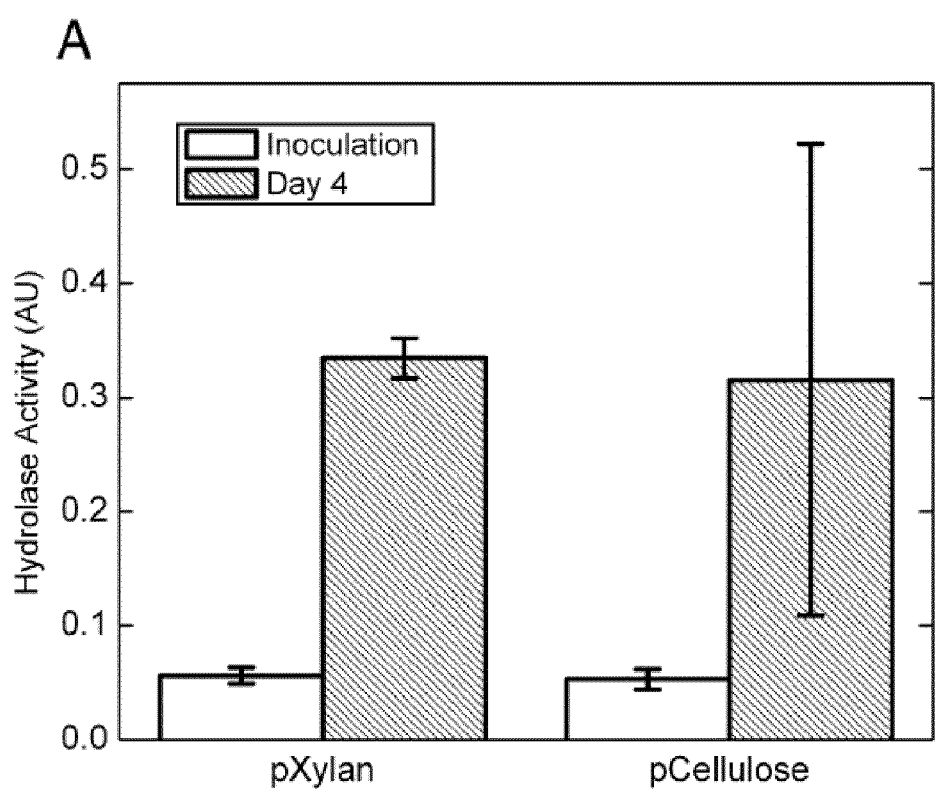
FIG. 9. Production of extracellular OsmY-Xyn10B and OsmY-Cel during growth on M9/switchgrass medium. A. Enzyme activities are measured using an azobeechwood xylan or azo-CMC assay on the day of inoculation or after 4 days of growth. B. SDS/PAGE gel of growth medium concentrated sevenfold taken from cultures indicated after 4 days of growth. BSA standards used to estimate protein concentrations are shown. For comparison, also shown are the cell lysate and sevenfold concentrated growth medium from a control strain grown for one day in MOPS/M9 0.16% glucose medium.
Figure 9B:
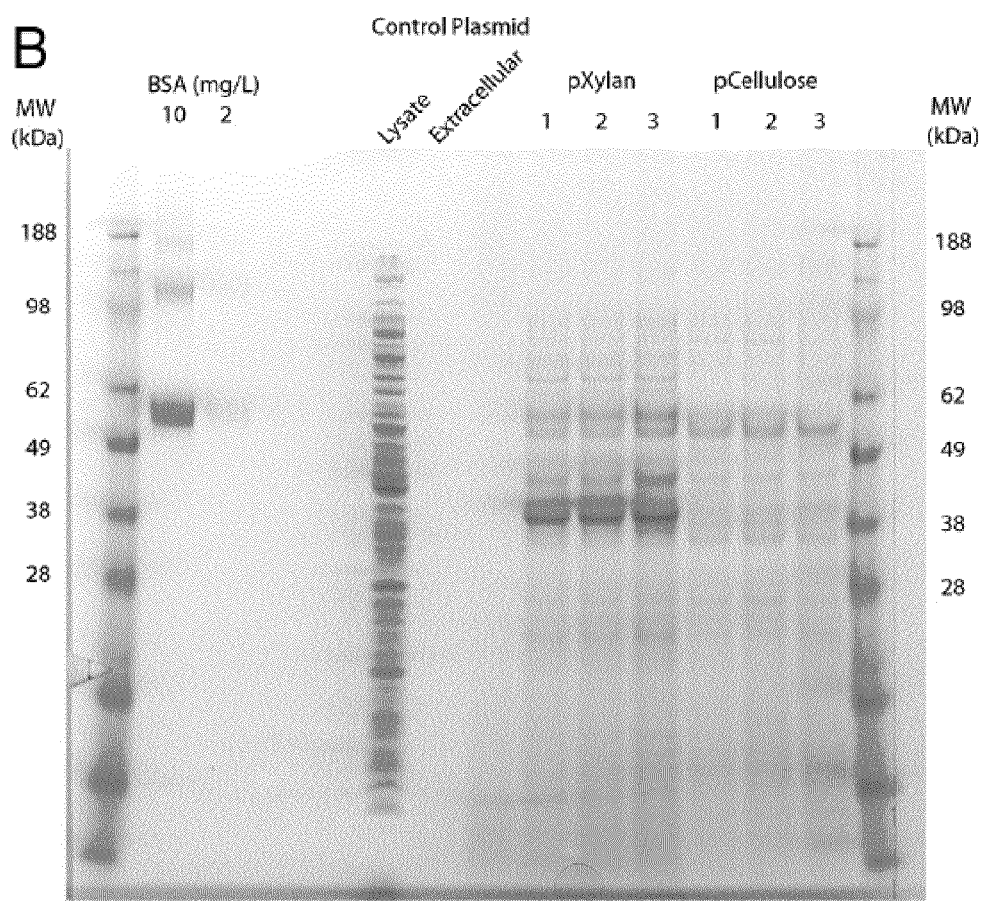

Next is an attempt to grow *E. coli* bearing either pXylan or pCellulose on plant biomass treated with the ionic liquid 1-ethyl-3-methylimidazolium acetate [$C_2$mim][OAc]. *E. coli* MG1655 strains bearing pXylan, pCellulose, or a control plasmid is inoculated into minimal medium containing 2.6% w/vol IL-treated switchgrass as the sole carbon source, without adding exogenous enzymes. The strains containing pXylan and pCellulose grow well, indicating that both the cellulose and hemicellulose components of the pretreated switchgrass can be used as carbon sources (FIG. 3D, red and green curves). The control strain shows minimal growth (FIG. 3D, black curve), indicating that most of the growth observed by the pCellulose and pXylan strains is enabled via enzymatic hydrolysis of cellulose and xylan, rather than any monosaccharides present in the switchgrass or released by pretreatment. The monocultures continue to produce up to 0.5 mg/L xylanase and cellulase enzymes during growth (FIG. 8). Leakage of other cellular proteins into the growth medium is observed, which may be a consequence of expressing fusions with a periplasmic protein (33) (FIG. 9). When the strains are combined and grown on switchgrass as a coculture, the cells grow to a cell density approximately equal to the sum of the individual monocultures (FIG. 3D, cyan curve), demonstrating growth on both fractions of switchgrass in one medium.

Growth on IL-pretreated *Eucalyptus globulus* is tested to determine if IL pretreatment renders a range of lignocellulose types digestible by the engineered *E. coli*. Both pXylan and pCellulose monocultures and a coculture of the two strains grow well in minimal medium containing 4.0% w/vol IL-treated eucalyptus (FIG. 3E). Finally, growth on IL-treated yard waste is tested, a feedstock that could avoid the costs of growing dedicated energy crops while decreasing landfill usage (34). Once again, both monocultures and coculture grow in minimal medium containing 2.6% w/vol yard waste (FIG. 3F).

To demonstrate production of advanced biofuels from plant biomass without the use of exogenously added GH enzymes, the biomass-consuming *E. coli* strains is engineered to generate three advanced biofuels directly from IL-treated switchgrass. Pathways that produce alcohols, linear hydrocarbons, or branched-chain hydrocarbons are chosen to test the integration of the biomass-consumption pathways with the extensive biosynthesis capabilities of *E. coli*. Biodiesel, typically made from plant oils that have been chemically esterified with methanol or ethanol, can also be made by *E. coli* in vivo in the form of fatty-acid ethyl esters (FAEE) (11). A six-gene FAEE production pathway is encoded on a single plasmid (pES120, FIG. 4A) and introduced the construct into a strain of *E. coli* MG1655 lacking the acyl-CoA dehydrogenase gene fadE. This strain is found to generate 405±27 mg/L from MOPS-M9/1% glucose (10 g/L) (or 0.04 g FAEE/g glucose, 12% of the theoretical yield of 0.33 FAEE/g glucose) (11), and 0.022 g FAEE/g xylose from 10 g/L xylose. *E. coli* MG1655 ΔfadE pES120 bearing pXylan or pCellulose produced FAEE from xylan or cellobiose, respectively (FIG. 10A), indicating that both strains are capable of FAEE production from their substrates. In order to produce FAEE from plant biomass, a coculture of both strains is grown in minimal medium containing 5.5% w/vol IL-treated switchgrass. The coculture produced 71±43 mg/L of FAEE, well above the no-carbon control (6.1±0.5 mg/L, FIG. 4B) and the noncellulolytic *E. coli* control (4±3 mg/L), indicating production of FAEE directly from pretreated switchgrass. This corresponds to 80% of the estimated yield obtainable with this pathway from the amount of sugars anticipated to be released from 5.5% switchgrass by the Cel and Xyn10B enzymes (0.14% glucose and 0.14% xylose).

Figure 4:
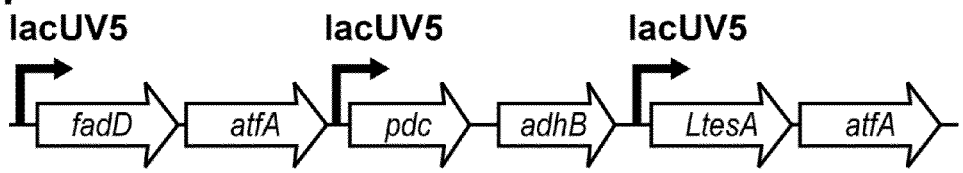
FIG. 4. Conversion of IL-treated switchgrass into advanced biofuels. (A) Gene schematics of plasmids encoding biofuel production pathways demonstrated in this work. Gene names listed in Table 2. Production of fatty-acid ethyl esters (B), butanol (C), and pinene (D) from IL-treated switchgrass by cocultures of cellulose- and xylan-consuming E. coli. Error bars represent standard deviation of biological triplicates.
Figure 4:
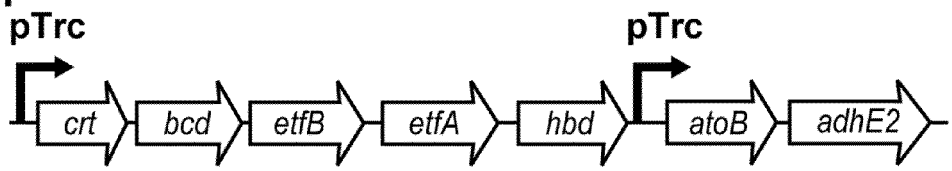
Figure 4:
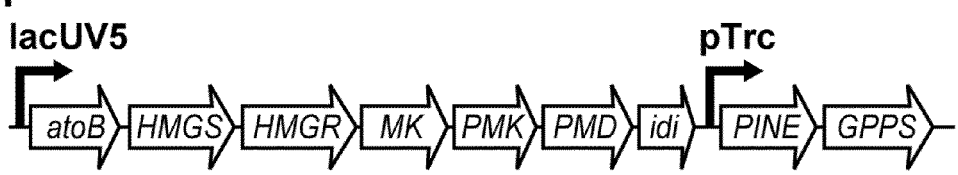
Figure 4:
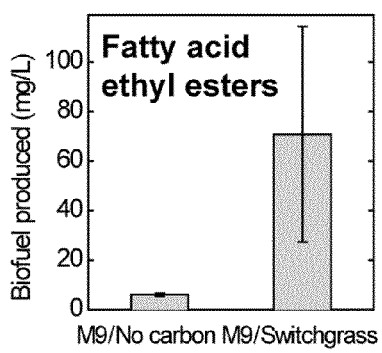
Figure 4:
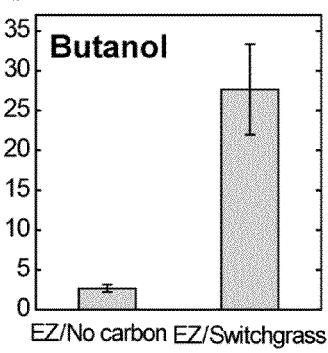
Figure 4:
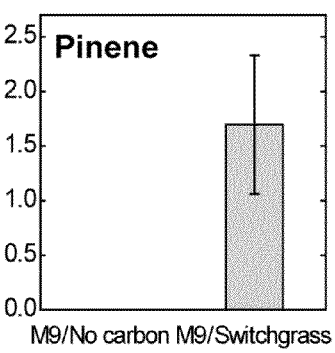
Figure 10:
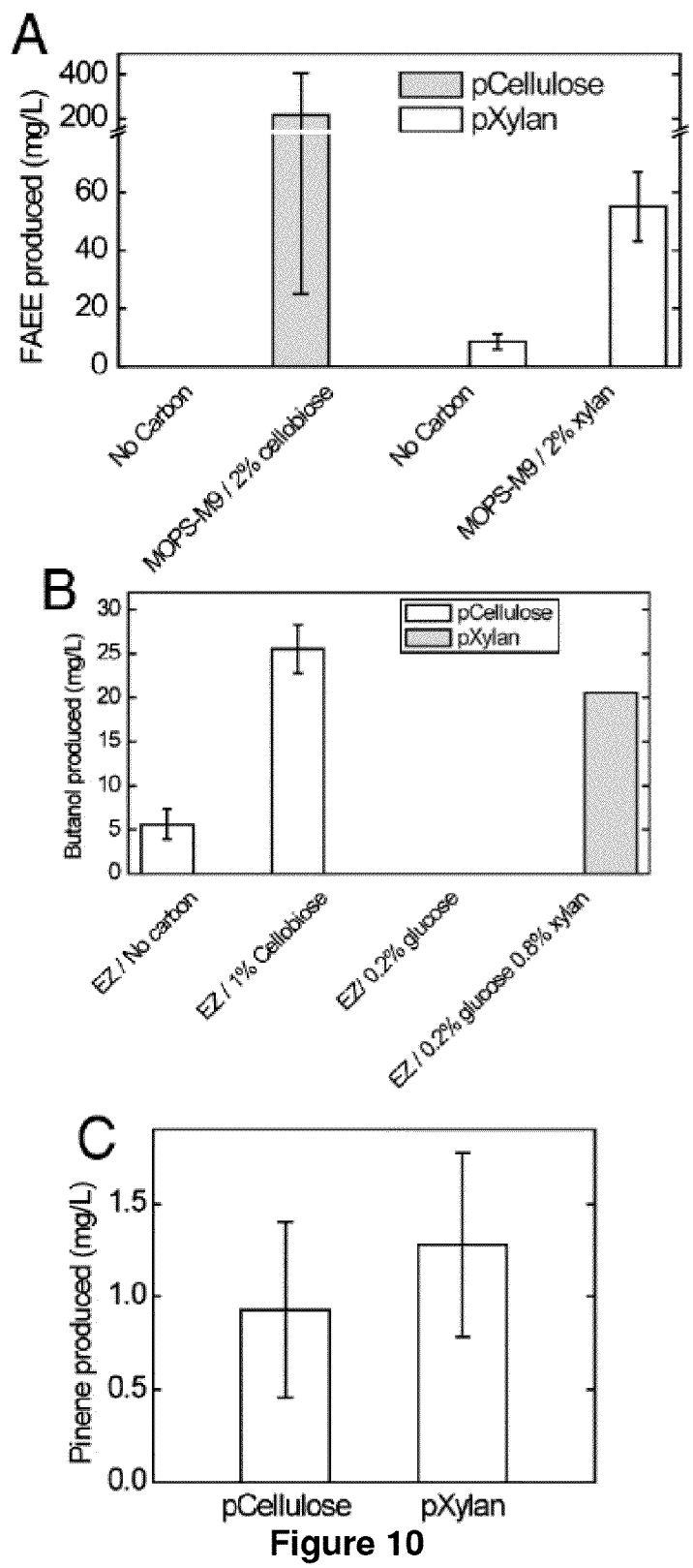
FIG. 10. Production of biofuels from either cellobiose or xylan by monocultures of pCellulose or pXylan. (A) Production of FAEE from either cellobiose or xylan by MG1655 ΔfadE pES120 bearing either pCellulose or pXylan, respectively, indicating that each strain is capable of producing FAEE from its substrate. Error bars represent standard deviation of biological triplicates. Overnight cultures grown in LB medium are inoculated 1/10 into 5 mL of MOPS-M9/2% cellobiose or beechwood xylan medium or medium with no carbon source. Cultures are induced with 50 µM IPTG after 1-2 days of growth, and produced FAEE are extracted 2 days after induction. All media are supplemented with 100 µg/mL carbenicillin and kanamycin. No FAEE are produced by MG1655 ΔfadE pES120 bearing pCellulose in medium without cellobiose. (B) Butanol produced by DH1 ΔadhE pButanol strains bearing either pCellulose or pXylan, from EZ-Rich medium containing either 1% cellobiose or 1% beechwood xylan, indicating that each strain is capable of producing butanol from its substrate. Production media are inoculated 1/20 from monocultures grown in LB medium and grown for several hours before induction with 200 µM IPTG. After induction the tubes are sealed with parafilm and moved to 30° C. Butanol is extracted after 2 days of production. All media are supplemented with 100 µg/mL carbenicillin and 30 µg/mL chloramphenicol. Error bars (pCellulose only) represent the standard deviation of biological triplicates. No butanol is detected in the EZ/0.2% glucose culture. (C) Pinene produced by MG1655 pPinene bearing either pCellulose or pXylan from cellobiose or xylan, respectively. Overnight cultures are inoculated 1/10 into 5 mL MOPS-M9 medium containing 2% cellobiose or beechwood xylan, or no carbon source at all, grown overnight, and induced with 200 IPTG. A dodecane overlay is applied and the cultures moved to 30° C. for 3 days before pinene is extracted from the dodecane. All media are supplemented with 100 µg/mL carbenicillin and 30 µg/mL chloramphenicol. No pinene is produced in medium without an added carbon source. Error bars represent standard deviation of biological triplicates.
Figure 11:
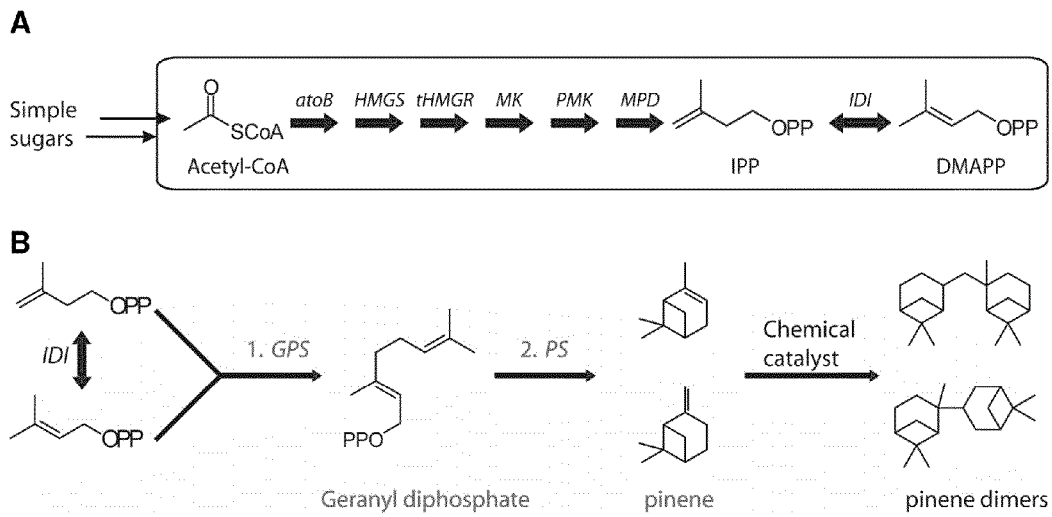
FIG. 11. The synthetic pathway of pinene.

Butanol has been proposed as a gasoline replacement because it is fully compatible with existing internal combustion engines. Based in part on previous work (9), a heterologous butanol pathway encoded on a single plasmid (pButanol, FIG. 4A) is constructed and inserted into an *E. coli* DH1 strain lacking the alcohol dehydrogenase gene, adhE. When bearing either pXylan or pCellulose, *E. coli* DH1 ΔadhE pButanol produces butanol from either xylan or cellobiose, respectively (FIG. 10B). A coculture of both strains yields 28±5 mg/L butanol from defined rich medium containing 3.3% w/vol IL-treated switchgrass as the main carbon source (FIG. 4C). A control strain lacking pXylan or pCellulose produces 8±2 mg/L butanol from pretreated switchgrass.

Finally, a metabolic pathway is constructed to produce the monoterpene pinene, an immediate chemical precursor to a potential jet fuel (35), directly from switchgrass. The pinene synthesis pathway is encoded on a single plasmid (pPinene, FIG. 4A) and introduced into *E. coli* MG1655. pXylan and pCellulose are combined into separate strains of *E. coli* MG1655 pPinene and confirmed that each strain is capable of producing pinene from either xylan or cellobiose, respectively (FIG. 10C). The strains are inoculated as a coculture into MOPS-M9 medium containing either 3.9% IL-treated switchgrass or no carbon source. The pinene pathway yields 1.7±0.6 mg/L pinene from pretreated switchgrass (FIG. 4D). No pinene is produced from a culture grown in MOPS-M9 medium without a carbon source or from switchgrass medium inoculated with a strain lacking pXylan or pCellulose.

Discussion

It is demonstrated the engineering of *E. coli* to produce three advanced biofuels suitable for existing fuel infrastructure directly from lignocellulosic plant biomass without using externally supplied GH enzymes. While the engineering is greatly facilitated by the tractability of *E. coli*, the approach described herein could be readily adapted for other microorganisms for use in a consolidated bioprocess to generate advanced biofuels from biomass. IL pretreatment using [$C_2$mim][OAc] renders three types of lignocellulose suitable for use by these strains as sole carbon sources, indicating that this system is likely applicable to lignocellulose feedstocks that are ecologically and economically appropriate to grow and harvest anywhere in the world. Overall, these results illustrate that the wide portfolio of compounds that can be synthesized by *E. coli*, or any other microorganism, can be produced directly from any IL-pretreated plant feedstock.

In order to make these *E. coli* strains suitable for use in an industrial bioprocess, both biofuel-producing and biomass-degrading capabilities require significant improvements. For instance, an optimal strain capable of producing FAEE at theoretical yield (0.33 g FAEE/1 g glucose) and achieving complete hydrolysis of IL-treated switchgrass, of which 78% is cellulose and xylan by weight (28), would obtain 0.26 g FAEE/1 g of IL-treated switchgrass, far higher than what could be achieved here. This requires an eightfold improvement in biofuel yield from glucose over what the current FAEE production pathway can achieve. More relevant to the engineered cellulolytic capabilities described herein, the cellulose and hemicellulose fractions (95% and 89%, respectively) not digested by the enzymes used here must be saccharified by the *E. coli* strain to achieve high biofuel yields or even to reach cell densities typical of an industrial fermentation process. A wide variety of enzymes found to have activity against IL-treated plant biomass is recently found in a cow rumen metagenome (36), and these enzymes could be screened to find either replacements for or supplements to the hydrolysis activity of Cel and Xyn10B enzymes. Furthermore, protein export pathways that do not compromise the cell membrane (as the OsmY fusions may be doing) should be used instead to avoid compromising cellular fitness and biofuel yields. Along with chromosomal integration of the biomass-consumption pathways (as opposed to encoding the pathways on plasmids), these steps should also improve the genetic stability of our modifications as well as their suitability for industrial-scale fermentations. In parallel with optimizations of the *E. coli* strain, the IL pretreatment could be modified to render the lignocellulose completely susceptible to hydrolysis by the GH enzymes we used here. For instance, acid catalysis during IL pretreatment of cellulose has been shown to dramatically increase the extent of subsequent enzymatic hydrolysis (37). These improvements will be required to fully realize the cost savings of a consolidated bioprocess that could provide a versatile platform for producing any advanced biofuel from any plant biomass at economical yields.

Materials and Methods

Selection, Optimization, and Screening of Cellulase Genes.

The set of cellulases is chosen to maximize diversity within family 5 endocellulases. First, the CAZy database is used to collate all known family 5 enzymes (38). The enzymes are aligned using Muscle (39) and then 10 are selected to maximize diversity using HyperTree (40). The 10 genes are then optimized for expression in *E. coli* using GeneDesigner and synthesized by DNA 2.0 (41). Two cultures each of *E. coli* DH10B cells bearing pGB012 plasmids encoding each individual OsmY-cellulase fusion are grown overnight in LB medium supplemented with 100 µg/mL carbenicillin and inoculated 1/100 into fresh LB. Cultures bearing pGB012 are used as a cellulase-free control. Cultures are grown at 37° C. to an optical density at 600 nm ($OD_{600}$) of 0.4 and induced by addition of IPTG to 200 µM, and expression proceeded at 37° C. for 20 h. As described herein, 200 µL of the supernatant is assayed for endocellulase activity.

Measurement of Native Promoter-Driven Cellulase Secretion.

*E. coli* MG1655 bearing plasmids with osmY-cel under control of several *E. coli* promoters is grown in LB medium (100 µg/mL carbenicillin) for 20 h before endocellulase activity present in the supernatant is measured.

Beta-Glucosidase Screening and Native Promoter Selection.

*E. coli* BL21 bearing beta-glucosidase genes is grown overnight in LB medium with 100 µg/mL carbenicillin, transferred 1/100 into M9/0.2% cellobiose medium with 100 µg/mL carbenicillin, and allowed to grow for 18 h at 37° C. before OD measurements are taken. A cell line bearing a plasmid with a beta-xylosidase is used as a control. For Cel3B-native promoter screening, plasmids bearing Cel3B under control of several *E. coli* promoters are introduced into *E. coli* BL21 cells, and transformants are grown in LB medium with 100 µg/mL carbenicillin overnight and inoculated 1/25 into a 96-well plate with 200 µL of M9/0.2% cellobiose medium or M9/0.2% glucose medium with 200 µg/mL carbenicillin. Growth is monitored with a microplate incubator and reader (TECAN). For Cel3A-native promoter screening, plasmids bearing Cel3A under control of one of several promoters are introduced into MG1655 cells, and overnight cultures are inoculated 1/40 into 800 µL of MOPS-M9/0.5% cellobiose or MOPS-M9/0.5% dextrose with 100 µg/mL carbenicillin in a 24-well plate. Growth is monitored with a microplate incubator and reader (TECAN).

Beta-Xylosidase Screening and Native Promoter Selection.

*E. coli* DH10B carrying beta-xylosidase genes under control of $P_{cspD}$ is grown overnight in LB medium with 100 µg/mL carbenicillin. The cultures do not grow at similar rates, likely due to the expression of proteins at toxic levels. Cultures are inoculated into MOPS-M9/0.2% xylan with 0.5 µg/mL thiamin and 100 µg/mL carbenicillin, into which sterile LB containing secreted OsmY-Xyn10B had been added (1/10 volume) to hydrolyze the xylan into xylodextrins. Growth is monitored on a 96-well plate with a microplate reader (TECAN). For Gly43F-native promoter screening, plasmids carrying gly43F under control of several *E. coli* promoters are introduced into *E. coli* MG1655 cells. Cells are grown overnight in LB medium with 100 µg/mL carbenicillin and inoculated 1/40 into 800 µL of MOPS-M9/0.5% beechwood xylan or xylose with 100 µg/mL carbenicillin supplemented with 5% of sterile LB containing secreted OsmY-Xyn10B on a 24-well plate. Growth is monitored with a microplate reader.

Growth Measurement on Beechwood Xylan.

Biological triplicates of *E. coli* MG1655 cells carrying either pXylan, $pP_{cstA}$-gly43Flp15A, or $pP_{cspD}$-osmY-xyn10B/SC101** is inoculated into LB with 100 µg/mL carbenicillin and grown at 37° C. for 16 h. Overnight cultures are inoculated 1/20 into 800 µL MOPS-M9/0.5% xylan or 0.5% xylose medium with 100 µg/mL carbenicillin and grown with shaking in a microplate reader (TECAN) at 37° C. Curves shown are averages of the triplicates, and median-averaged over a five-point window.

Growth Curves on Biomass and PASC.

For biomass medium, IL-treated biomass (prepared as described herein) is washed with water to remove any growth inhibitors present (such as residual IL). A full description of washing procedure can be found in herein. 10 mL of MOPS-M9 with biomass and 100 µg/mL carbenicillin is used as growth medium. For growth on PASC, triplicates of *E. coli* MG1655 bearing plasmids pCellulose, $pP_{wrbA}$-cel3A/p15A, or $p(P_{csD}$-RBS3-osmY-cel/ISC101**) are grown overnight in LB with 100 µg/mL carbenicillin. For growth on plant biomass, *E. coli* MG1655 bearing either plasmid pXylan, pCellulose, or a control plasmid are grown for 18 h at 37° C. in LB medium containing 100 µg/mL carbenicillin. For growth of monocultures on biomass, the biomass medium is inoculated 1/20 (0.5 mL) with either the control, pXylan, or pCellulose cultures. For growth of pXylan/pCellulose cocultures, the biomass medium is inoculated with 0.25 mL pXylan and pCellulose cultures. All growth curves are performed with biological triplicates (three different colonies), with the exception of the yard waste control culture, which is performed in duplicate. Growth is measured by serially diluting a sample $10^{-6}$ (2 µL in 200 µL three times) in sterile phosphate-buffered saline, and 100 µL of the $10^{-6}$ dilution is spread on an LB-agar plate. Colonies are counted the next day.

Conversion of Switchgrass to FAEE.

Three aliquots of 5 mL MOPS-M9 medium containing either 5.5% sterilized washed switchgrass or no carbon source are prepared and inoculated 1/20 with cultures of *E. coli* MG1655 ΔfadE pES120 with either pXylan or pCellulose (or 1/10 with control culture) grown for 24 h in LB medium. Cultures are grown at 37° C. for 92 h, at which point FAEE production is induced by addition of 50 µM IPTG. The production cultures are left at room temperature for 4 h after induction and returned to 37° C. for 96 h of production time. Free fatty-acid ethyl esters, and free fatty acids, are measured largely as described in ref. 11.

Conversion of Switchgrass to Butanol.

Twelve cultures of 5-mL EZ-Rich medium (Teknova) are prepared as described by the manufacturer except without glucose. Six of the cultures contained 3.3% (w/vol) washed, IL-treated switchgrass. *E. coli* DH1 ΔadhE pButanol carrying pCelluose or pXylan is grown in LB medium for 38 or 25 h, respectively, at 37° C. Biomass and null media are inoculated with 0.25 mL of each culture (0.5 mL total inoculum size) and cultures moved to 37° C. for 6.5 h, after which 2 mL of EZ-Rich salts (to final concentration, including original formulation, of 2×) is added to the cultures. Cultures are grown at 30° C. and induced after 30 min by addition of 200 µM IPTG, sealed with parafilm (creating a microaerobic environment), and returned to 30° C. for 96 h. Butanol is extracted and quantified as described herein.

Conversion of Switchgrass to Pinene.

Twelve aliquots of 5 mL MOPS-M9 medium, six of which contained 3.9% (w/vol) washed switchgrass, are prepared. Three overnight cultures each of *E. coli* MG1655/pPinene carrying a control plasmid, pXylan or pCellulose are grown for 24 h in LB medium. 0.5 mL of control culture, or 0.25 mL of both pXylan and pCellulose, is added to the switchgrass and null media and the cultures grown at 37° C. After 22 h, pinene production is induced by addition of 200 µM IPTG, 0.55 mL dodecane is added to trap the pinene, and the cultures are incubated to 30° C. for 72 h. Extraction and quantification of pinene is performed as described herein.

Minimal Medium Preparation.

M9 medium is prepared using M9 salts (Sigma) with the addition of 2 mM $MgSO_4$ and 0.1 mM $CaCl_2$, plus antibiotics as described below. MOPS-M9 medium (Teknova) is prepared as per the manufacturer's instructions, except the carbon source (glucose) is replaced by other sugars or carbon sources as described.

Strains and Cloning.

*E. coli* strain DH10B (Invitrogen) is used for bacterial transformation and plasmid amplifications. Other *E. coli* strains are used as described below. *E. coli* strain MG1655 ΔfadE is constructed using homologous recombination with the Lambda Red system (42) using primers GEB040110-dFadE.f and GEB040110-dFadE.r to amplify the kanamycin resistance gene from the plasmid pKD13 with homology arms to the region nearby the fadE gene. *E. coli* strain DH1 ΔadhE is constructed with the Lambda Red system using primers F9 and F10* to amplify the kanamycin resistance gene from pKD13 with homology arms targeting the adhE gene.

Cloning of pGB012 Plasmid for Enzyme Export.

The osmY gene (native sequence) is amplified from synthetic DNA (DNA 2.0) using the primers GEB030309-OsmY-nolink-BamHI.rev and GEB030309-OsmY-Bgl2.for and digested with the restriction enzymes BglII and XhoI. The digested product is ligated into BglII-XhoI-digested plasmid pBbE5a-RFP, producing the plasmid pGB012. pGB012 is digested with BamHI and XhoI, enabling genes digested with BglII and XhoI to be ligated into pGB012, generating protein fusions with OsmY joined to the N terminus via a glycine-serine linker, as per the BglBrick standard (43)

Cloning of Cellulase Genes into pGB012 for Cellulase Screening.

Cellulase genes (0-9) are amplified from the synthetic gene library received from DNA 2.0. PCR fragments are digested with BglII and XhoI and ligated into BamHI/XhoI-digested pGB012

Cloning of cel and xyn10B into pGB012.

Cel and Xyn10B are amplified from synthetic DNA (DNA 2.0) using the primers GEB030909-BB-Cel7.for and GEB030909-BB-Cel7.rev (for Cel7) and GEB030909-BB-XynB.for and GEB030909-BB-XynB.rev (for Xyn10B). PCR products are digested with BglII and XhoI and ligated into pGB012 digested with BamHI and XhoI Construction of Plasmids for *E. coli* Promoter-Driven Expression.

A fragment of pBbA5a-RFP is amplified using primers GEB052209-RK.for and GEB052209-RK.rev. Promoters are amplified from *E. coli* MG1655 genomic DNA using the primers below, and promoters and plasmid are joined using the sequence- and ligation-independent cloning method (SLIC) (44), replacing the lacI gene and the lacUV5 promoter with the native promoter while retaining the rfp gene downstream. Promoter-RFP plasmids are subsequently digested with BglII-XhoI to remove the rfp gene, and are ligated with BglII-XhoI-digested genes (OsmY-Cel7, OsmY-Xyn10B, beta-glucosidase genes, and beta-xylosidase genes).

Cloning of Beta-Glucosidases and Xylobiosidases from *Cellvibrio japonicus*.

Beta-glucosidases and xylobiosidases are amplified from the genomic DNA of *C. japonicus* NCIMB 10462, and the PCR products digested using BglII and XhoI and ligated into BglIIXhoI-digested pBbE5a-RFP (beta-glucosidase genes) or the plasmid pPcspD-rfp/p15A digested with BglII-XhoI (betaxylosidase genes).

Construction of pXylan Plasmid.

PcspD-osmY-xyn10B is transferred to plasmid pBbS5a by amplifying PcspD-osmY-xyn10B from plasmid pPcspD-osmY-xyn10B/p15A with the primers GEB090909-SlicAmpR. for and GEB072709-SLIC-XhoI-term.rev, and pBbS5a amplified using GEB090909-SlicAmpR.rev and GEB072709-SLIC-XhoI-term.for. The two fragments are joined using SLIC, and a fragment bearing PcspD-osmY-xyn10B with the SC101_ori and part of the bla antibiotic resistance marker is amplified using primers GEB032910-T3-CspDp.F and GEB090909-SlicAmpR. rev. A terminator ("triple terminator") is amplified from plasmid pNS26σVL (4) using the primers GEB032910-T3-CspDp.R and GEB032910-Gly43F-T3.F. PcstA-gly43F is amplified from the plasmid pPcstA-gly43F/p15A using the primers GEB032910-Gly43F-T3.R and GEB090909-SlicAmpR.for. These three fragments are joined together using one-step isothermal in vitro recombination (46).

Construction of pCellulose Plasmid.

PcspD-rfp is introduced onto plasmid pBbS5a by amplifying PcspD-rfp using the primers GEB090909-SlicAmpR.for and GEB072709-SLIC-XhoI-term.-rev, and the pBbS5a backbone using GEB090909-SlicAmpR.rev and GEB072709-SLIC-XhoMerm.for, and joining the fragments together using SLIC. PcspD-osmY-cel with a somewhat weaker ribosome binding site is constructed by amplifying osmY-cel with primers GB042610-OsmYRBS3.F and GEB030909-BBCel7. rev, digested with BglII/XhoI, and ligated into BglII/XhoIdigested plasmid pPcspD-rfp/SC101_, making plasmid pð PcspDRBS3-osmY-cel/SC101_Þ. PcspD-RBS3-osmY-cel is amplified with the SC101_ ori and part of the bla gene using the primers GEB032910-T3-CspDp.F and GEB090909-SlicAmpR.rev. The triple terminator is amplified from plasmid pNS2σVL using the primers GEB032910-T3-CspDp.R and GEB032910-Cel3AT3.F. PwrbA-cel3A is amplified from the plasmid pPwrbA-cel3A/p15A using the primers GEB032910-Cel3A-T3.F and GEB090909-SlicAmpR.rev, and joined together with the triple terminator fragment using PCR SOEing (47). The fragment PwrbA-cel3A-triple terminator is joined with PcspD-RBS3-osmYcel via SLIC.

Construction of pES120.

pLacUV5 is amplified using primers that add BglII (5') and XhoI (3') sites and digested with the restriction enzymes BglII and XhoI. The digested product is ligated into BglII-XhoI-digested plasmid pKS104 (7), producing plasmid pES104.

The pdc and adhB genes from pKS13 (48) are amplified using primers pdc-bb-for and adhB-bb-rev and digested with the restriction enzymes BglII and XhoI. The digested product is ligated into BglII-XhoI-digested plasmid pES104, producing plasmid pES105. The previous pLacUV5 digested product is ligated into BglII-XhoI-digested plasmid pES105, producing pES106. LtesA (48) is amplified using the primers LtesAbb-for and LtesA-bb-rev and digested with BglII and XhoI. The digested product is ligated into BglII-XhoI-digested plasmid pES106, producing plasmid pES107. The previous pLacUV5 digested product is ligated into BglII-XhoI-digested plasmid pES107, producing pES109. The gene aftA (48) is amplified using the primers atfA-bb-for and atfA-bb-rev and the product is subsequently digested with BglII and XhoI and ligated into BglII-XhoI-digested pES109, producing pES114. Finally, the three-operon, 6-gene cassette is cloned into plasmid pBbE5k-RFP.

Construction of pButanol.

The *C. acetobutylicum* butyryl-CoA biosynthetic operon—crt, hbd, etfAB, hbd genes—is amplified from *C. acetobutylicum* ATCC824 genomic DNA (ATCC) using primers F76/F73. The *C. acetobutylicum* alcohol dehydrogenase adhE2 gene is amplified using primers F72/F74; primer F72 included a synthetic ribosome binding site with estimated translation initiation rate of 50,000 (arbitrary units) (49). The vector backbone containing a p15A origin, chloramphenicol selective marker, Ptrc promoter and gene encoding for LacIQ is amplified using primers F75/F77. The three PCR products are assembled using SLIC, producing plasmid pBMO49. A copy of *E. coli* atoB and an additional Ptrc promoter are inserted before adhE2. atoB is PCR amplified off the *E. coli* chromosome using primers F92/F93; primer F92 contained a synthetic ribosome binding site with estimated translation initiation rate of 100,000 (arbitrary units). The Ptrc promoter is PCR amplified using primers F90/F91. The vector backbone is digested with restriction enzymes BglII and BamHI, and subsequently assembled with the Ptrc and atoB PCR products using the SLIC protocol, producing plasmid pBM050, referred to here as pButanol.

Construction of pPinene.

pBbA5c-MevT-MBI is prepared by ligation of pBbA5c-MevT vector (BamHI/XhoI) and BglBrick compatible MBI insert (BglII/XhoI) by standard BglBrick cloning strategy using compatible BglII and BamHI restriction sites. Individual genes in mevalonate pathway are PCR amplified from pMevT and pMBI (50) with primers contain EcoRI and BglII sites at 5'-end and BamHI and XhoI sites at 3'-end of each gene. The BglBrick restriction sites found in each gene are removed by site-specific mutagenesis. Both MevT and MBI are constructed separately by sequential standard BglBrick ligation in pBbA5c vector (BglBricked vector with p15A origin, PlacUV5 promoter, and chloramphenicol resistant), and combined to generate pBbA5c-MevT-MBI. The geranyl pyrophosphate synthase (GPPS) from *Abies grandis* and the pinene synthase (PS) from *Pinus taeda* are codon optimized for *E. coli* and synthesized (Genescript). The GPPS and the PS are cloned into pTRC99, plastid signal peptides removed, between NcoI and XmaI using primer pairs PPY630/PPY608 and PPY642/PPY643, respectively, to generate plasmids pGPPS and pPS. The plasmid pPS-GPPS is constructed by amplifying the GPPS from pGPPS using primer pair PPY674/PPY652 and introducing it into pPS between BamHI and HindIII via SLIC. The GPPS and PS genes with the PTRC promoter are amplified from pPS-GPPS using primers GB090110-PinepTrc. For and GB082010-Pine.R-evseq, digested with BglII and XhoI, and ligated into a BamHI-XhoI digested pBbA5c-MevT-MBI to create pPinene.

Assay for Secreted Endocellulase and Endoxylanase Activity.

200 µL of culture medium is added to 200 µL, of 2% azo-carboxymethycellulose (S-ACMCL, Megazyme) or azobeechwood xylan (S-AXBL). Reactions are incubated at 37° C. for 15 min before quenching by addition of 1 mL of precipitant solution (0.4 M sodium acetate, 75% ethanol). Quenched reactions are centrifuged to pellet the undigested CMC or xylan precipitate, and enzyme activity measured by determining the absorbance (590 nm) of the liberated Remazolbrilliant Blue R dye.

Biomass Saccharification by OsmY-Xyn10B and OsmY-Cel.

0.25 mL sterile-filtered LB medium containing secreted OsmYXyn10B or OsmY-Cel is added to 10 mL MOPS-M9 medium with 3.5% switchgrass with 1.5 mM sodium azide. Digestion reactions are performed at 37° C. with shaking and 0.5 mL samples are taken every 24 h. Samples are analyzed by HPLC using a Agilent 1200 Series equipped with a Bio-Rad Aminex HPX-87H ion exclusion column (300 mm×7.8 mm, catalog number 125-0140), using 4 mM$H_2SO_4$ in water as a running buffer at 0.6 mL/minute with a temperature of 50° C. Oligo- and monosaccharides are detected using a refractive index monitor. Composition of IL-treated switchgrass is taken from reference (28).

PASC Preparation.

PASC is prepared largely as described (51), with some modifications. 1 gram of autoclaved Avicel PH-101 (Fluka) is suspended in 3 mL of sterile deionized $H_2O$, dissolved in 50 mL phosphoric acid (87%) and stirred at 4° C. overnight. 100 mL of sterile cold $H_2O$ is added to the solution, causing the cellulose to precipitate. The cellulose is centrifuged and washed repeatedly with cold sterile $H_2O$, and 2.5 mL of 2 M sodium carbonate is added. The cellulose is washed again repeatedly until the pH of the solution is measured to be ~7.

$[C_2mim][OAc]$ Ionic Liquid Pretreatment of Biomass.

1-Ethyl-3-methylimidazolium acetate $[C_2mim][OAc]$, BASF, purity ≥90%) is used as the ionic liquid. *Eucalyptus globulus* is supplied by Arborgen. Yard waste (FIG. S6) is gathered from a residential back yard in Berkeley, Calif. Biomass is milled and sieved to a particle size of 250-400 µm (40-60 mesh). Moisture is removed by drying to constant weight in a convection oven at 40° C. A 5% loading of biomass to ionic liquid is used (10 g biomass to 190 g $[C_2mim][OAc]$). The biomass and IL are placed in a 450 mL borosilicate vessel, which is placed in a Parr Instrument Company Mini Bench Top Reactor (part no. 4562). The reactor is purged of air using N2 and the reactants stirred at 300 rpm and heated to 120° C. with venting. At temperature the reactor is sealed and the reaction allowed to proceed for 3 h. Temperature ramp and cooling (to 30° C.) times are approximately 15 and 30 min respectively. Three parts $H_2O$ to one part reactant is then added to the cooled reactant whilst stirring vigorously, causing precipitation of the biomass. The precipitated components are filtered for subsequent processing.

Biomass Preparation.

Ten to 35 grams of biomass precipitated from ionic liquid pretreatment is centrifuged and resuspended at least six times with 200 mL deionized $H_2O$ to remove toxic ionic liquid and collected over Miracloth (Calbiochem). Excess water is squeezed from the biomass, and the biomass is added to culture tubes. Some wet biomass is placed into preweighed Eppendorf tubes, weighed, lyophilized for at least 2 days, and reweighed to determine the amount of dry biomass solids.

Water is added to the biomass in the culture tubes and the tubes are sterilized in an autoclave for 20-40 minutes in a liquid cycle. After cooling, MOPS-M9 salts, other nutrients, and antibiotics are added to the biomass.

Yield Estimation of FAEE from Glucose and Xylose.

Triplicate cultures of *E. coli* MG1655 ΔfadE pES120 with a control plasmid are grown overnight in LB medium with 100 μg/mL carbenicillin and 100 μg/mL kanamycin and inoculated 120 into 5 or 6 mL of MOPS-M9/1% glucose or xylose, respectively, and grown at 37° C. FAEE production is induced with 50 uM IPTG when cultures reached OD of ~0.6. FAEE is extracted and measured after 72-96 hours of production as described in ref. 48.

Estimate of Concentration of Secreted Proteins.

Cell-free supernatants are taken from monocultures of MG1655/pXylan or MG1655/pCellulose grown for 100 hours on MOPS-M9/2.6% ILtreated switchgrass, or from a control culture grown in MOPSMO/0.16% glucose, and concentrated sevenfold using 3,000 MWCO spin filters (Millipore, catalog number UFC500396). NuPage LDS loading buffer and reducing reagent (Invitrogen) are added and proteins denatured at 70° C. for 15 minutes before loading. BSA standards (NEB) are diluted and treated identically. Samples are run on a 4-12% BIS-TRIS NuPage gel (Invitrogen) in MES-SDS buffer and stained using Gelcode Blue Safe stain (Thermo Scientific). The gel image is analyzed using ImageJ software to obtain lane profiles. The intensities of the most intense bands observed in each supernatant are obtained by fitting regions of the lane profiles to a Gaussian distribution. Bands in the BSA lanes are used to calibrate protein concentrations.

Extraction and Quantification of Butanol.

Butanol is extracted from 750 μL of culture by adding 750 μL ethyl acetate and vigorously mixing the phases. The ethyl acetate contains 0.05% pentanol as an internal standard. The ethyl acetate phase is analyzed with gas chromatography on a Focus GC (Thermo Scientific) equipped with a Triplus autosamper and a flame ionization detector maintained at 250° C. Separation occurred on a TR-WAX capillary column (Agilent Technologies) with helium as the carrier gas at 300 kPa using the following program: initial temperature 45° C. for 1.5 minutes, followed by a 15° C./minute ramp to 90° C., followed by a 30° C. ramp to 120° C.

Extraction and Quantification of Pinene.

Quantification of α-pinene is performed by gas chromatography/mass spectrometry (GC/MS) using authentic α-pinene (Across). After identifying the microbially produced pinene in MS full scan mode m/z 136 and 121 are chosen for selective ion monitoring. The organic layer is analyzed by GC/MS (Polaris Q Trace GC Ultra) equipped with a TR-5MS capillary column (30 m×0.25 mm internal diameter, 0.25 μM film thickness, Thermo Scientific). The gas chromatography program used is 70° C. for 1 min, then ramping 35° C. min-1 to 150, and 40° C. min-1 to 250° C.

TABLE 2

Key to gene designations in FIG. 9

| Gene Name | Full name | Source organism | Reference |
|---|---|---|---|
| fadD | long chain fatty acid CoA-ligase | E. coli | (1) |
| atfA | wax ester synthase | A. baylyi ADP1 | (1) |
| pdc | pyruvate decarboxylase | Z. mobilis ZM4 | (1) |
| adhB | alcohol dehydrogenase | Z. mobilis ZM4 | (1) |
| LtesA | thioesterase ("leaderless" tesA) | E. coli | (1) |
| crt | crotonase | C. acetylbutylicum | (2) |
| bcd | butyryl-CoA dehydrogenase | C. acetylbutylicum | (2) |
| etfB | electron transport flavoprotein B | C. acetylbutylicum | (2) |
| etfA | electron transport flavoprotein A | C. acetylbutylicum | (2) |
| hbd | 3-hydroxybutyryl-CoA dehydrogenase | C. acetylbutylicum | (2) |
| atoB | acetyl-CoA acetyltransferase | E. coli | (2) |
| adhE2 | aldehyde/alchol dehydrogenase | C. acetylbutylicum | (2) |
| HMGS | hydroxymethylglutaryl-CoA synthase | S. cerevisiae | (3) |
| HMGR | hydroxymethylglutaryl-CoA reductase | S. cerevisiae | (3) |
| MK | mevalonate kinase | S. cerevisiae | (3) |
| PMK | phosphomevalonate kinase | S. cerevisiae | (3) |
| PMD | phosphomevalonate decarboxylase | S. cerevisiae | (3) |
| idi | isopentenyl pyrophosphate isomerase | E. coli | (3) |
| PINE | pinene synthase | P. taeda | (4) |
| GPPS | geranyl pyrophosphate synthase | A. grandis | (5) |

(1) Steen E J, et al. (2010) Microbial production of fatty-acid-derived fuels and chemicals from plant biomass. Nature 463: 559-562.
(2) Atsumi S, et al. (2008) Metabolic engineering of *Escherichia coli* for 1-butanol production. Metabolic Engineering 10: 305-311.
(3) Martin V J J, Pitera D J, Withers S T, Newman J D, Keasling J D (2003) Engineering a mevalonate pathway in *Escherichia coli* for production of terpenoids. Nat Biotechnol 21: 796-802.
(4) Phillips M A, Wildung M R, Williams D C, Hyatt D C, Croteau R (2003) cDNA isolation, functional expression, and characterization of (+)-alpha-pinene synthase and (−)-alpha-pinene synthase from loblolly pine (*Pinus taeda*): Stereocontrol in pinene biosynthesis. Arch Biochem Biophys 411: 267-276.
(5) Burke C, Croteau R (2002) Geranyl diphosphate synthase from *Abies grandis*: cDNA isolation, functional expression, and characterization. Arch Biochem Biophys 405: 130-136.

Example 2

Construction of GPPS and PS Fusion Protein and Pinene Using Engineered *Escherichia coli*

Table 3 shows exemplary operons of GPPS and PS (e.g. pTrcPtPS-PtGPPS) and protein fusions of these enzymes (pTrcPtPS-(GSG)$_2$PtGPPS). When the GPPS and PS are from the same species, the fusion proteins synthesize higher levels of pinene compared to the operons. For example, host cells with pTrc-AgPS-AgGPPS produce 2 mg/L of pinene, while host cells with pTrc-AgGPPS-(GSG)$_2$-AgPS produce 14 mg/L of pinene. The fusion proteins with GPPS and PS from the same species synthesize higher levels of pinene compared to the fusion proteins with GPPS and PS from different species.

TABLE 13

Plasmids encoding GPPS and PS fusion proteins

| | | | Pinene synthase Gymnosperm Mn | | | |
|---|---|---|---|---|---|---|
| | | | *Pinus taeda* | *Abies grandis* | *Picea abies* | *Pinus taeda* (−) |
| GPPs | Gymno-sperm | *Pinus taeda* | pTrc-PtPS-PtGPPS (681) vs. pTrc-PtGPPS-(GSG)2-PtPS | pTrc-AgPS-PtGPPS (684) vs. pTrc-PtGPPS-(GSG)2-AgPS (659) | pTrc-PaPS-PtGPPS (675) vs. pTrc-PtGPPS-(GSG)2-PaPS (660) | pTrc-PtPS(−)-PtGPPS vs. pTrc-PtGPPS-(GSG)2-PtPS(−) |
| | | *Abies grandis* | pTrc-PtPS-AgGPPS (711) vs. pTrc-AgGPPS-(GSG)2-PtPS (661) | pTrc-AgPS-AgGPPS (710) vs. pTrc-AgGPPS-(GSG)2-AgPS (530) | pTrc-PaPS-AgGPPS (728) vs. pTrc-AgGPPS-(GSG)2-PaPS (673) | pTrc-PtPS(−)-AgGPPS vs. pTrc-AgGPPS-(GSG)2-PtPS(−) |
| | | *Picea abies* | pTrc-PtPS-PaGPPS (680) vs. pTrc-PaGPPS-(GSG)2-PtPS | pTrc-AgPS-PaGPPS (683) vs. pTrc-PaGPPS-(GSG)2-AgPS (670) | pTrc-PaPS-PaGPPS (674) vs. pTrc-PaGPPS-(GSG)2-PaPS (658) | pTrc-PtPS(−)-PaGPPS vs. pTrc-PaGPPS-(GSG)2-PtPS(−) |
| | Angio-sperm | *Artemisia annua* | pTrc-PtPS-AaGPPS vs. pTrc-AaGPPS-(GSG)2-PtPS | pTrc-AgPS-AaGPPS vs. pTrc-AaGPPS-(GSG)2-AgPS | pTrc-PaPS-AtGPPS vs. pTrc-AtGPPS-(GSG)2-PaPS | pTrc-PtPS(−)-AaGPPS vs. pTrc-AaGPPS-(GSG)2-PtPS(−) |
| | | *Arabidopsis thaliana* | pTrc-PtPS-AtGPPS (682) vs. pTrc-AtGPPS-(GSG)2-PtPS (390) | pTrc-AgPS-AtGPPS (685) vs. pTrc-AtGPPS-(GSG)2-AgPS | pTrc-PaPS-AtGPPS (676) vs. pTrc-AtGPPS-(GSG)2-PaPS | pTrc-PtPS(−)-AtGPPS vs. pTrc-AtGPPS-(GSG)2-PtPS(−) |

Figure 12:
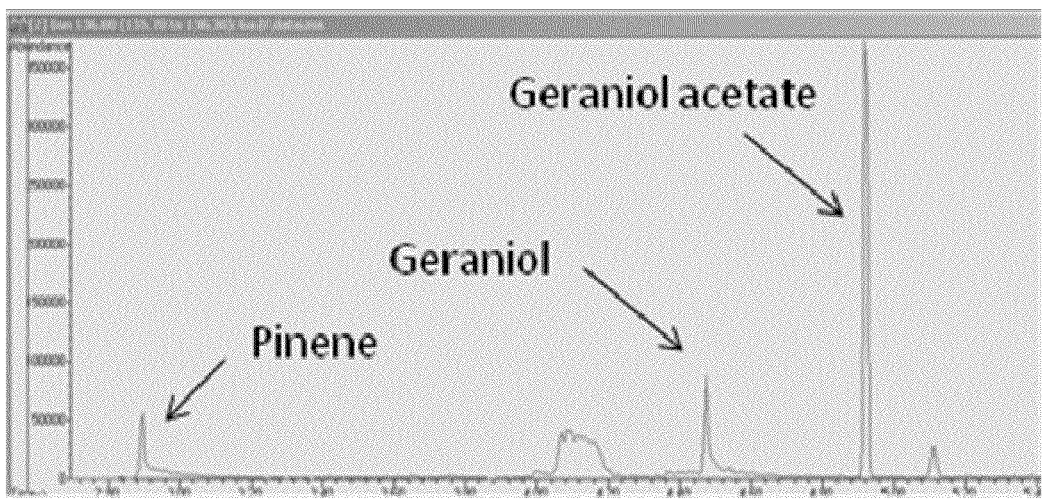
FIG. 12. Relative amounts of pinene, geraniol and geraniol acetate produced.

FIG. 12 shows that pinene synthase is the rate limiting step in pinene synthesis.

Figure 13:
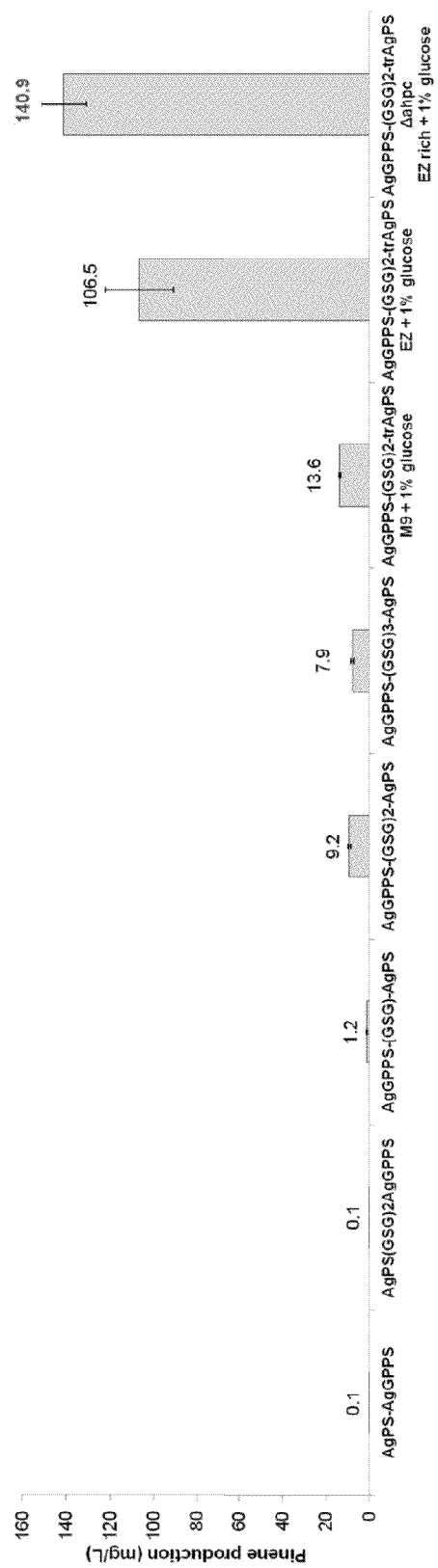
FIG. 13. Pinene production using different operon and protein fusions.

FIG. 13 shows that a 6 amino acid long linker provide a high level of pinene synthesis. The first column from the left shows that the operon of PS and GPPS from the same species leads to 0.1 mg/L (minimal media, 1% glucose). The third column from the left shows the correct order of GPPS-PS fusion leads to an increase from 0.1 to 1.2 mg/L (minimal media, 1% glucose). The fourth column from the left shows the correct GPPS-PS fusion length (6 amino acids) leads to an increase from 1.2 to 9.2 mg/L (minimal media, 1% glucose). The sixth column from the left shows the truncation of Ps in GPPS-PS fusion leads to an increase from 9.2 to 13.6 mg/L (minimal media, 1% glucose). The second column from the right shows using the same construct in rich defined media the pinene production rises from 13.6 to 106 mg/L. The first column from the right shows using the same construct in rich defined media in a strain with more manganese pinene production rises from 106 to 140 mg/L.

Figure 14:
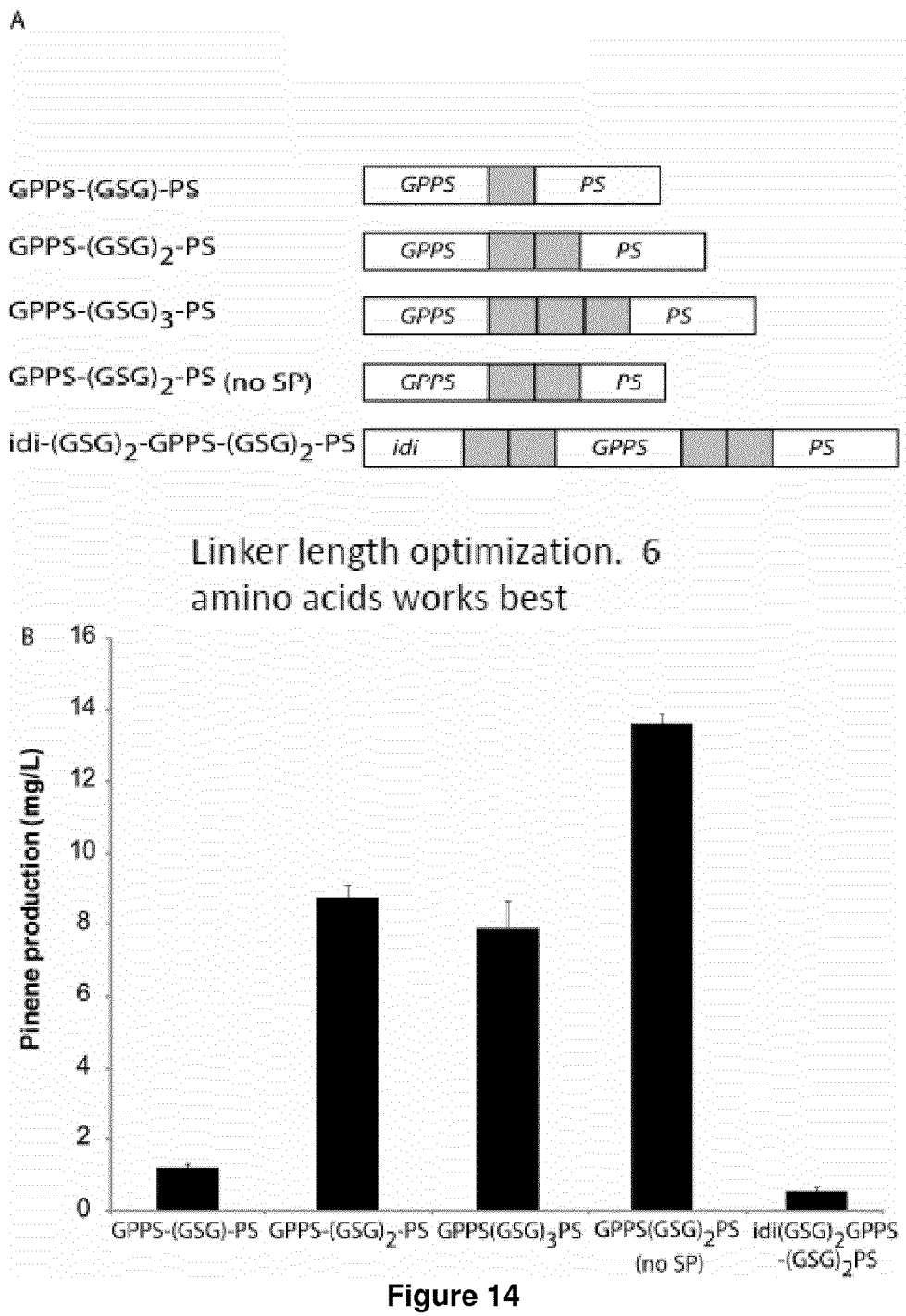
FIG. 14. (A) Different GPPS-PS fusion protein constructs with different linkers. (B) Pinene production using the different constructs.

FIG. 14 shows that using a 6 amino acid long linker works best of the different linkers tested.

Figure 15:
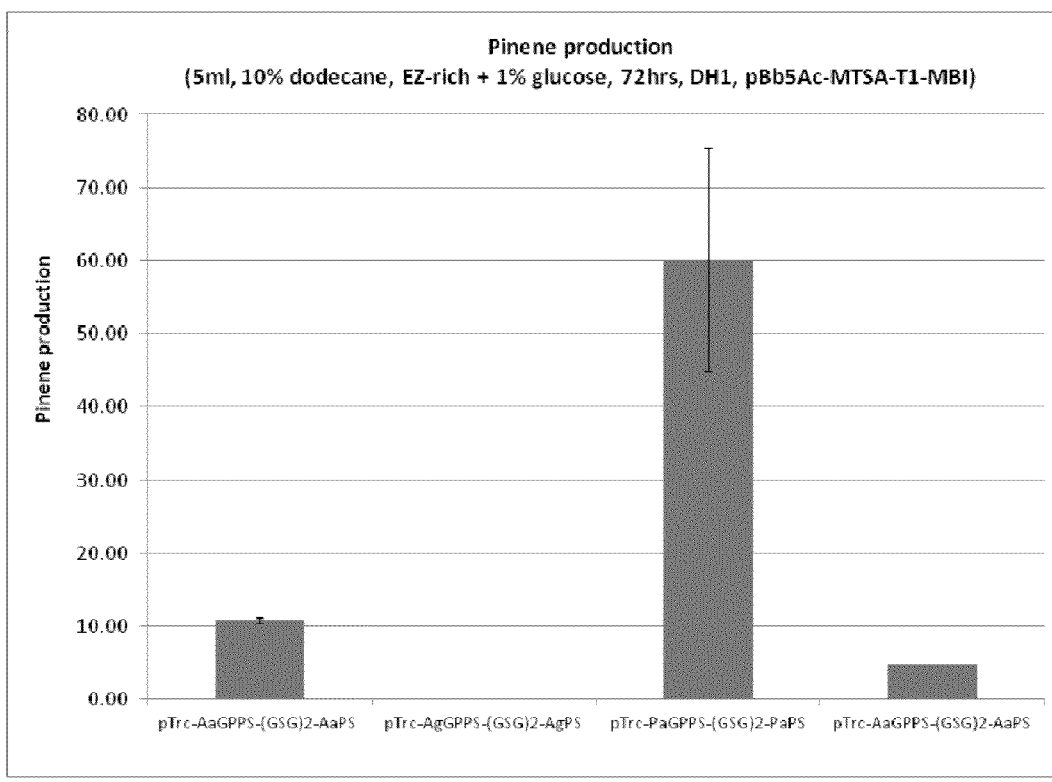
FIG. 15. Pinene production using protein fusions with GPPS/PS from different species.

FIG. 15 shows that that fusion proteins from certain species produce higher levels of pinene compared to fusion proteins from other species.

Figure 16:
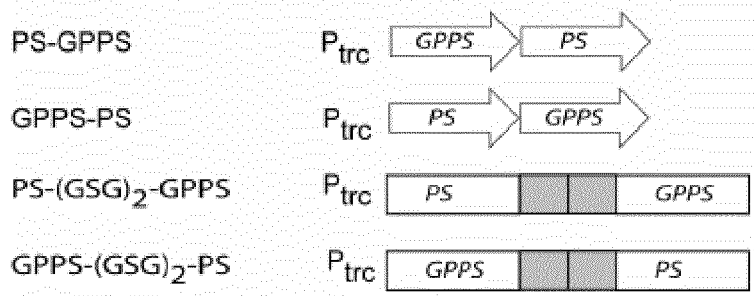
FIG. 16. (A) Different GPPS-PS operon and fusion protein constructs. (B) Pinene production using the different constructs.
Figure 16:
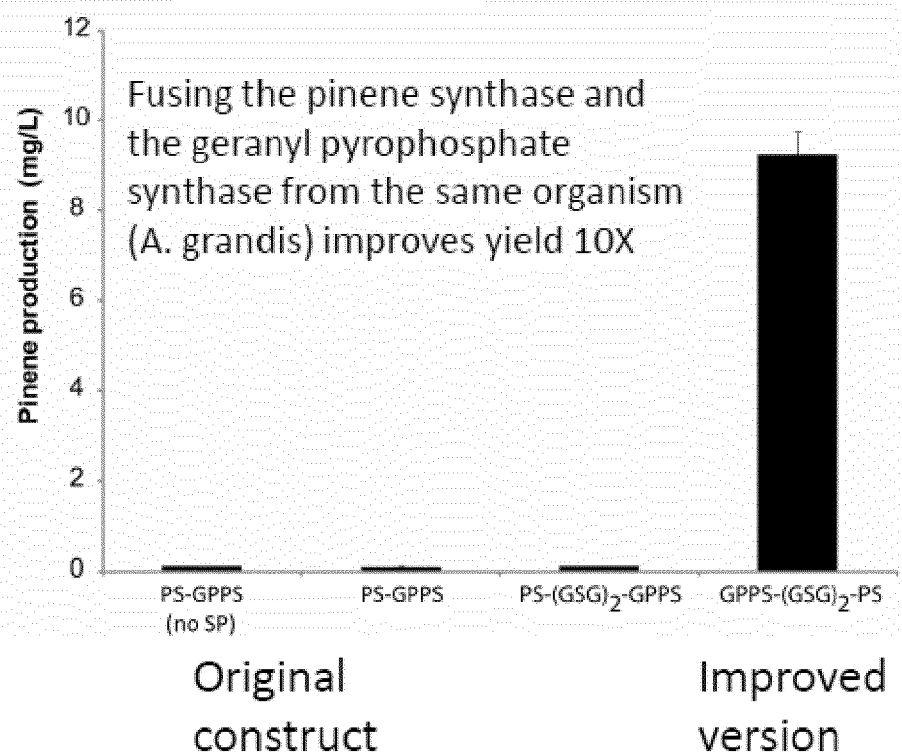

FIG. 16 shows that fusion proteins with GPPS linked to N-terminus of PS via a linker produced higher levels of pinene compared to the other configurations tested.

The conditions used for pinene production are always the same (100 μM IPTG, 72 hrs). These are the optimal conditions identified for pBbA5c-MevT-MBI but may not be the best ones for pBbA5c-MTSA-T1-MBI (fixed). pBbA5c-MTSA-T1-MBI (fixed) is used because it leads to productions of over 400 mg/L of limonenene, another monoterpene.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A fusion protein comprising: (a) a pinene synthase (PS), or enzymatically active fragment thereof, and (b) a geranyl pyrophosphate synthase (GPPS), or enzymatically active fragment thereof, wherein the C-terminus of (b) is linked to the N-terminus of (a), and (a) and (b) are linked by a linker which is a peptide of between 3 and 9 amino acid residues; wherein the PS is a *Pinus taeda*, *Picea abies*, or *Abies grandis* PS; and the GPPS is a *Picea abies* or *Abies grandis* GPPS.

2. The fusion protein of claim 1, wherein the linker is a peptide of between 5 and 7 amino acid residues.

3. The fusion protein of claim 2, wherein the linker is a peptide of 6 amino acid residues.

4. The fusion protein of claim 3, wherein the peptide of 6 amino acid residues has the amino acid sequence GSGGSG (SEQ ID NO:1).

5. The fusion protein of claim 1, wherein the PS is a *Picea abies* or *Abies grandis* PS.

6. The fusion protein of claim 1, wherein the GPPS is an *Abies grandis* GPPS.

7. The fusion protein of claim 1, wherein the PS and GPPS are from a same species.

8. The fusion protein of claim 7, wherein the species is *Picea abies*.

9. The fusion protein of claim 7, wherein the species is *Abies grandis*.

* * * * *